(12) United States Patent
Kohlman et al.

(10) Patent No.: US 7,312,236 B2
(45) Date of Patent: Dec. 25, 2007

(54) SUBSTITUTED (4-AMINOCYCLOHEXEN-1-YL)PHENYL AND (4-AMINOCYCLOHEXEN-1-YL)PYRIDINYL COMPOUNDS AS 5-HT$_{1F}$ AGONISTS

(75) Inventors: Daniel Timothy Kohlman, Camby, IN (US); Frantz Victor, Indianapolis, IN (US); Yao-Chang Xu, Fishers, IN (US); Bai-Ping Ying, Fishers, IN (US); Deyi Zhang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 104 days.

(21) Appl. No.: 10/576,762

(22) PCT Filed: Dec. 6, 2004

(86) PCT No.: PCT/US2004/038226

§ 371 (c)(1),
(2), (4) Date: Apr. 21, 2006

(87) PCT Pub. No.: WO2005/061439

PCT Pub. Date: Jul. 7, 2005

(65) Prior Publication Data

US 2007/0078169 A1    Apr. 5, 2007

(51) Int. Cl.
C07D 213/75 (2006.01)
C07C 233/80 (2006.01)
A61K 31/44 (2006.01)
A61K 31/165 (2006.01)

(52) U.S. Cl. ............ 514/352; 514/336; 514/340; 514/617; 546/268.1; 546/309; 564/184

(58) Field of Classification Search ............ 546/268.1, 546/309; 564/184; 514/336, 352, 340, 617
See application file for complete search history.

(56) References Cited

U.S. PATENT DOCUMENTS

| | | | |
|---|---|---|---|
| 5,521,196 | A | 5/1996 | Audia et al. |
| 5,521,197 | A | 5/1996 | Audia |
| 5,708,187 | A | 1/1998 | Flaugh et al. |
| 5,721,252 | A | 2/1998 | Audia et al. |
| 5,814,653 | A | 9/1998 | Flaugh et al. |
| 6,384,034 | B2 * | 5/2002 | Simitchieva et al. .. 514/252.01 |

FOREIGN PATENT DOCUMENTS

| WO | WO 96/29075 | 9/1996 |
|---|---|---|
| WO | WO 97/13512 | 4/1997 |
| WO | WO 98/08502 | 3/1998 |
| WO | WO 98/15545 | 4/1998 |
| WO | WO 98/20875 | 5/1998 |
| WO | WO 98/46570 | 10/1998 |
| WO | WO 98/55115 | 10/1998 |
| WO | WO 99/25348 | 5/1999 |
| WO | WO 00/00487 | 1/2000 |
| WO | WO 00/00490 | 1/2000 |
| WO | WO 00/34266 | 6/2000 |
| WO | WO 00/47559 | 8/2000 |
| WO | WO 00/50426 | 8/2000 |
| WO | WO 03/008455 A1 | 1/2003 |
| WO | WO 03/008494 A1 | 10/2003 |

OTHER PUBLICATIONS

Adham, N, et a.l., "Cloning of another human serotonin receptor (5-HT$_{1F}$): A fifth 5-HT$_1$ receptor subtype coupled to the inhibition of adenylate cyclase", *Proc, Natl, Acad. Sci USA*, vol. 90-408-412, 1993.

* cited by examiner

Primary Examiner—Zinna N. Davis
(74) Attorney, Agent, or Firm—R. Craig Tucker

(57) ABSTRACT

The present invention relates to compounds of formula I:

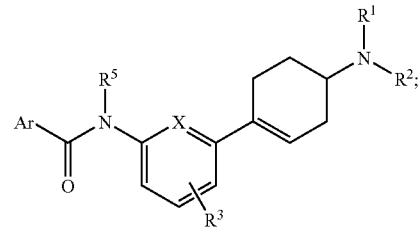

or a pharmaceutically acceptable acid addition salt thereof, where;

X is —C(R$^4$)═ or —N═;
Ar is phenyl, substituted phenyl, heterocycle, or substituted heterocycle;
R$^1$ and R$^2$ are independently hydrogen or C$_1$-C$_3$ alkyl;
R$^3$ is hydrogen, fluoro, or methyl;
when X is —C(R$^4$)═, R$^4$ is hydrogen, fluoro, or methyl, provided that no more than one of R$^3$ and R$^4$ may be other than hydrogen; and
R$^5$ is hydrogen, methyl, or ethyl. The compounds of the present invention are useful for activating 5-HT$_{1F}$ receptors, inhibiting dural protein extravasation, and for the treatment or prevention of migraine in a mammal.

10 Claims, No Drawings

SUBSTITUTED (4-AMINOCYCLOHEXEN-1-YL)PHENYL AND (4-AMINOCYCLOHEXEN-1-YL)PYRIDINYL COMPOUNDS AS 5-HT$_{1F}$ AGONISTS

BACKGROUND OF THE INVENTION

Until recently, theories regarding the pathophysiology of migraine have been dominated since 1938 by the work of Graham and Wolff. *Arch. Neurol. Psychiatry*, 39:737-63, 1938. They proposed that the cause of migraine headache was vasodilatation of extracranial vessels. This view was supported by knowledge that ergot alkaloids and sumatriptan, a hydrophilic 5-HT$_1$ agonist which does not cross the blood-brain barrier, induce contraction of cephalic vascular smooth muscle and are effective in the treatment of migraine. Humphrey, et al., *Ann. NY Acad. Sci.*, 600:587-600, 1990. Recent work by Moskowitz has shown, however, that the occurrence of migraine headaches is independent of changes in vessel diameter. *Cephalalgia*, 12:5-7, 1992.

Moskowitz has proposed that currently unknown triggers for pain stimulate trigeminal ganglia that innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers. *Neurology*, 43(suppl. 3):S16-S20 1993. Sumatriptan, in fact, has high affinity for the 5-HT$_{1B}$ and 5-HT$_{1D}$ receptors, K$_i$=10.3 nM and 5.1 nM, respectively, which activity may be indicative of vasoconstrictive activity. Sumatriptan and similar compounds previously advanced for the treatment of migraine had tended to be selected on the basis of this vasoconstrictive activity under the premises of the prior art models for migraine.

Serotonin (5-HT) exhibits diverse physiological activity mediated by at least seven receptor classes, the most heterogeneous of which appears to be 5-HT$_1$. A human gene which expresses one of these 5-HT$_1$ receptor subtypes, named 5-HT$_{1F}$, was isolated by Kao and coworkers. *Proc. Natl. Acad. Sci. USA*, 90:408-412, 1993. This 5-HT$_{1F}$ receptor exhibits a pharmacological profile distinct from any serotonergic receptor yet described. It was found that sumatriptan, in addition to the above mentioned strong affinities for the 5-HT$_{1B}$ and 5-HT$_{1D}$ receptors, also has affinity for the 5-HT$_{1F}$ receptor subtype, with a K$_i$ of about 23 nM. This suggests a possible role for the 5-HT$_{1F}$ receptor in migraine.

Various 5-HT$_{1F}$ receptor agonists have subsequently been developed which have shown relative selectivity for the 5-HT$_{1F}$ receptor subclass and it has been shown that such selectivity generally reduces the vasoconstrictive activity characteristic of other compounds advanced as potential agents for the treatment of migraine and associated disorders.

Included among these 5-HT$_{1F}$ receptor agonists are compounds disclosed in the following:

U.S. Pat. Nos. 5,708,187 and 5,814,653, describing a family of 6-substituted-3-amino(alkyl)-tetrahydrocarbazoles and 7-substituted-4-amino(alkyl)cyclohepta(7, 6b)Indoles;

U.S. Pat. No. 5,521,196, U.S. Pat. No. 5,721,252, U.S. Pat. No. 5,521,197, and WO 96/29075, describing various families of 5-substituted piperidin-3-yl-indoles and 5-substituted 1,2,3,6 tetrahydropyridin-3-yl-indoles;

WO 97/13512 describing a family of 5-substituted 3-aminoethylindoles;

WO 98/46570 describing a family of 5-substituted indoles, pyrrolo(3,2-b)pyridines, benzofurans, and benzothiophenes, having the 3-position substituted with octahydroindolizinyl, octahydro-2H-quinolizinyl, decahydropyrido(1,2-a)azepinyl, 1,2,3,5,8,8a-hexahydroindolizinyl, 1,3,4,6,9,9a-hexahydro-2H-quinolizinyl, or 1,4,6,7,8,9,10,10a-octahydropyrido(1,2-a) azepinyl;

WO 98/20875 and WO 99/25348 describing two families of 5-substituted piperidin-3-yl-azaindoles and 5-substituted 1,2,3,6-tetrahydropyridin-3-yl-azaindoles;

WO 00/00487 describing a family of 5-substituted (piperidin-3-yl or 1,2,3,6-tetrahydropyridin-3-yl)indoles, azaindoles, benzofurans, and benzothiophenes;

WO 98/08502 describing a family of 8-substituted-1,2,3, 4-tetrahydro-2-dibenzofuranamines and 9-substituted-2-aminocyclohepta(b)benzofurans;

WO 98/55115 describing a family of 3-amino-1,2,3,4-tetrahydro-9H-carbazole-6-carboxamides and 4-amino-10H-cyclohepta(7,6-b)indole-7-carboxamides;

WO 98/15545 describing a select family of 3,5-disubstituted indoles and benzofurans;

WO 00/00490 describing a family of 5-allyl-substituted (piperidin-3-yl or 1,2,3,6-tetrahydropyridin-3-yl)indoles, azaindoles, benzofurans, and benzothiophenes;

WO 00/47559 describing a family of 4-(3-substituted-benzoyl)piperidines;

WO 00/50426 describing a family of 3,5-disubstituted azabenzofurans;

WO 00/34266 describing a family of 3-heteroaryl-5-(2-(aryl or heteroaryl)-2-oxoethyl)indoles; and WO 03/08455 describing a family of pyridinoylpiperidines.

Continued research has now surprisingly yielded a new and unexpected class of novel selective 5-HT$_{1F}$ agonists having distinct chemical and receptor binding properties, which inhibit dural protein extravasation, while avoiding significant vasoconstrictive activity, and are therefore useful for the treatment of migraine and other 5-HT$_{1F}$ receptor associated disorders.

SUMMARY OF THE INVENTION

The present invention relates to substituted (4-aminocyclohexen-1-yl)phenyl and (4-aminocyclohexen-1-yl)pyridinyl compounds of the general formula I:

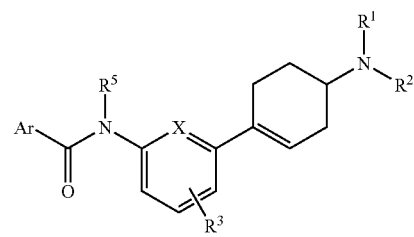

or pharmaceutically acceptable acid addition salts thereof, where:

X is —C($R^4$)= or —N=;

Ar is phenyl, substituted phenyl, heterocycle, or substituted heterocycle;

$R^1$ and $R^2$ are independantly hydrogen or $C_1$-$C_3$ alkyl;

$R^3$ is hydrogen, fluoro, or methyl;

when X is —C($R^4$)=, $R^4$ is hydrogen, fluoro, or methyl, provided that no more than one of $R^3$ and $R^4$ may be other than hydrogen;

$R^5$ is hydrogen, methyl, or ethyl.

The present invention also relates to pharmaceutical compositions comprising a compound of formula I, or a pharmaceutically acceptable acid addition salt thereof, and a pharmaceutically acceptable carrier, diluent, or excipient. In another embodiment, the present invention relates to pharmaceutical compositions adapted for the activation of 5-$HT_{1F}$ receptors, for the inhibition of dural protein extravasation, and/or for the treatment or prevention of migraine in mammals, particularly humans, containing a compound of formula I, or a pharmaceutically acceptable acid addition salt thereof, and a pharmaceutically acceptable carrier, diluent, or excipient.

In addition, the present invention relates to a method for activating 5-$HT_{1F}$ receptors in mammals, particularly humans, comprising administering to a mammal in need of such activation an effective amount of a compound of formula I, or a pharmaceutically acceptable acid addition salt thereof.

Moreover, the present invention relates to a method for inhibiting dural protein extravasation in mammals, particularly humans, comprising administering to a mammal in need of such inhibition an effective amount of a compound of formula I, or a pharmaceutically acceptable acid addition salt thereof.

Additionally, the present invention relates to a method for treating or preventing migraine in mammals, particularly humans, comprising administering to a mammal in need of such treatment or prevention, an effective amount of a compound of formula I, or a pharmaceutically acceptable acid addition salt thereof.

Another aspect of the present invention relates to the use of a compound of formula I as a medicament, and in particular a medicament adapted for the activation of 5-$HT_{1F}$ receptors, for the inhibition of dural protein extravasation, and/or for the treatment or prevention of migraine in mammals, particularly humans. That is to say, the present invention relates to the use of a compound of formula I for the activation of 5-$HT_{1F}$ receptors, for the inhibition of dural protein extravasation, and/or for the treatment or prevention of migraine in mammals, particularly in humans.

Additionally, the present invention relates to the use of one or more compounds of formula I in the manufacture of a medicament for the activation of 5-$HT_{1F}$ receptors, for the inhibition of dural protein extravasation, and/or for the treatment or prevention of migraine in mammals, particularly in humans.

Furthermore, the present invention provides for methods for the treatment and/or prevention of 5-$HT_{1F}$-mediated disorders comprising administering to a mammal in need of such treatment or prevention, particularly a human, an effective amount of a compound of formula I, or a pharmaceutically acceptable acid addition salt thereof. In preferred embodiments, the 5-$HT_{1F}$-mediated disorder is dural protein extravasation and/or migraine.

DETAILED DESCRIPTION OF THE INVENTION

The following detailed description is provided to aid those skilled in the art in practicing the present invention. Even so, the following description should not be construed to unduly limit the present invention in that modifications and variations in the embodiments discussed herein can be made by those of ordinary skill in the art without departing from the spirit or scope of the present inventive discovery. Such modifications and variations are contemplated as being within the scope of the invention.

One embodiment of the present invention is a method for increasing activation of 5-$HT_{1F}$ receptors, while avoiding vasoconstrictive activity, for treating a variety of disorders that have been linked to decreased neurotransmission of serotonin in mammals. Included among these disorders are migraine, general pain, trigeminal neuralgia, dental pain or temperomandibular joint dysfunction pain, anxiety, general anxiety disorder, panic disorder, depression, disorders of sleep, chronic fatigue syndrome, premenstrual syndrome or late luteal phase syndrome, post-traumatic syndrome, memory loss, dementia including dementia of aging, social phobia, autism, attention deficit hyperactivity disorder, disruptive behavior disorders, impulse control disorders, borderline personality disorder, obsessive compulsive disorder, premature ejaculation, erectile dysfunction, bulimia, anorexia nervosa, alcoholism, tobacco abuse, mutism, and trichotillomania. The compounds of this invention are also useful as a prophylactic treatment for migraine. Any of these methods employ a compound of formula I. In preferred embodiments, the mammal to be treated by the administration of the compounds of formula I is human.

In those instances where the disorders which can be treated by serotonin agonists are known by established and accepted classifications, their classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

The use of a compound of formula I for the activation of the 5-$HT_{1F}$ receptor, for the inhibition of dural protein extravasation, in general or due to stimulation of the trigeminal ganglia specifically, and/or for the treatment of any of the disorders described above, are all embodiments of the present invention. In one preferred embodiment, the invention provides a method for the treatment of migraine in a mammal, as for example a human, comprising administering to a mammal in need of such treatment, a pharmaceutically effective amount of a compound of formula I. In another preferred embodiment, the invention provides a method for the prevention of migraine in a mammal, as for example a human, comprising administering to a mammal in need of such treatment, a pharmaceutically effective amount of a compound of formula I.

Likewise, the use of a compound of formula I, or a combination of more than one compound of formula I, in the manufacture of a medicament for the activation of the 5-HT$_{1F}$ receptor, for the inhibition of dural protein extravasation, in general or due to stimulation of the trigeminal ganglia specifically, and/or for the treatment of any of the disorders described above, are also all embodiments of the present invention.

The general chemical terms used throughout have their usual meanings. For example, the term alkyl refers to a branched or unbranched saturated hydrocarbon group. The term "n-alkyl" refers to an unbranched alkyl group. By way of illustration, but without limitation, the term "$C_1$-$C_2$ alkyl" refers to methyl and ethyl. The term "$C_1$-$C_3$ n-alkyl" refers to methyl, ethyl, and n-propyl. The term "$C_1$-$C_3$ alkyl" refers to methyl, ethyl, n-propyl, and isopropyl. The term "$C_1$-$C_4$ alkyl" refers to methyl, ethyl, n-propyl, isopropyl, n-butyl, isobutyl, sec-butyl, and t-butyl. The term "$C_1$-$C_6$ alkyl" refers to all branched and unbranched alkyl groups having from one to six carbon atoms. The term "$C_2$-$C_6$ alkyl" refers to all branched and unbranched alkyl groups having from two to six carbon atoms. The term "$C_3$-$C_6$ cycloalkyl" refers to cyclopropyl, cyclobutyl, cyclopentyl, and cyclohexyl. The term "$C_3$-$C_7$ cycloalkyl" also includes cycloheptyl. Cycloalkylalkyl refers to a cycloalkyl moiety linked through an n-alkyl chain, as for example, but not limited to, "$C_3$-$C_6$ cycloalkyl-$C_1$-$C_3$ alkyl," which refers to a $C_3$-$C_6$ cycloalkyl moiety linked through a 1 to 3 carbon n-alkyl chain. Each alkyl, cycloalkyl, and cycloalkylalkyl group may be optionally substituted as provided for herein.

The terms "alkoxy", "phenyloxy", "benzyloxy" and "pyrimidinyloxy" refer to an alkyl group, phenyl group, benzyl group, or pyrimidinyl group, respectively, each optionally substituted as provided for herein, that is bonded through an oxygen atom.

The terms "alkylthio", "phenylthio", and "benzylthio" refer to an alkyl group, phenyl group, or benzyl group, respectively, each optionally substituted as provided for herein, that is bonded through a sulfur atom.

The term "$C_1$-$C_4$ acyl" refers to a formyl group or a $C_1$-$C_3$ alkyl group bonded through a carbonyl moiety. The term "$C_1$-$C_4$ alkoxycarbonyl" refers to a $C_1$-$C_4$ alkoxy group bonded through a carbonyl moiety.

The term "halo" refers to fluoro, chloro, bromo, or iodo. Preferred halo groups are fluoro, chloro, and bromo. More preferred halo groups are fluoro and chloro.

The term "heterocycle" is taken to mean a saturated or unsaturated 5- or 6-membered ring containing from 1 to 3 heteroatoms selected from nitrogen, oxygen and sulfur, said ring optionally being benzofused. Exemplary heterocycles, for the purposes of the present invention, include furanyl, thiophenyl, pyrrolyl, pyridinyl, N-methylpyrrolyl, pyrimidinyl, pyrazinyl, benzofuranyl, benzothiophenyl, indolyl, and the like, all of which may be optionally substituted, which also includes optionally substituted on the benzo ring when the heterocycle is benzofused.

Substituted alkyl, cycloalkyl, cycloalkylalkyl, alkoxy, or alkylthio, means an alkyl, cycloalkyl, cycloalkylalkyl, alkoxy, or alkythio group, respectively, substituted one or more times independently with a substituent selected from the group consisting of halo, hydroxy, and $C_1$-$C_3$ alkoxy. Preferred substitutions include substitution 1-5 times with halo, each independently selected, or substituted 1-3 times with halo and 1-2 times independently with a group selected from hydroxy and $C_1$-$C_3$ alkoxy, or substituted 1-3 times independently with a group selected from hydroxy and $C_1$-$C_3$ alkoxy, provided that no more than one hydroxy and/or alkoxy substituent may be attached through the same carbon.

The terms "substituted phenyl" and "substituted heterocycle" are taken to mean that the cyclic moiety in either case is substituted with one to five, preferably one to three halo substituents; or substituted with one to two substituents independently selected from the group consisting of halo, $C_1$-$C_4$ alkyl, $C_1$-$C_4$ alkoxy, $C_1$-$C_4$ alkylthio, cyano, and nitro, wherein each alkyl, alkoxy and alkylthio substituent can be further substituted independently with one to five halo groups each independently selected from fluoro, chloro, and bromo. When a substituent is halo, preferred halo groups are fluoro and chloro.

Abbreviations used herein are defined as follows:
Anal. cal'd means calculated elemental analysis;
BINAP means 2,2'-bis(diphenylphosphino)-1,1'binaphthyl.
DCM means dichloromethane;
DMF means N,N-dimethylformamide.
DMSO means dimethylsulfoxide.
ES means electron spray;
EtOAc means ethyl acetate
EtOH means ethanol;
MeOH means methanol;
MS means mass spectrum;
n-BuLi means n-butyl lithium
Pd$_2$(dba)$_3$ means tris(dibenzylideneacetone)dipalladium (0)
Pd(OAc)$_2$ means palladium (II) acetate.
p-TsOH means para-toluenesulfonic acid.
THF means tetrahydrofuran.

The term "amino protecting group" as used in this specification refers to a substituent commonly employed to block or protect the amino functionality while reacting other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), t-butoxycarbonyl (t-BOC), and the like; and like amino protecting groups. The species of amino protecting group employed is not critical so long as the derivatized amino group is stable to the conditions of subsequent reactions on other positions of the molecule and can be removed at the appropriate point without disrupting the remainder of the molecule. The selection and use (addition and subsequent removal) of amino protecting groups is well known within the ordinary skill of the art. Further examples of groups referred to by the above terms are described by T. W. Greene and P. G. M. Wuts, "Protective Groups in Organic Synthesis", 3$^{rd}$ edition, John Wiley and Sons, New York, N.Y., 1999, chapter 7, hereafter referred to as *"Greene"*.

The term "pharmaceutical" or "pharmaceutically acceptable" when used herein as an adjective, means substantially non-toxic and substantially non-deleterious to the recipient.

By "pharmaceutical composition" it is further meant that the carrier, solvent, excipients and salt must be compatible with the active ingredient of the composition (e.g. a compound of formula I). It is understood by those of ordinary skill in this art that the terms "pharmaceutical formulation" and "pharmaceutical composition" are generally interchangeable, and they are so used for the purposes of this application.

The term "acid addition salt" refers to a salt of a compound prepared by reaction of the compound with a mineral or organic acid. The compounds of the present invention form pharmaceutically acceptable acid addition salts with a wide variety of organic and inorganic acids and include the physiologically acceptable salts which are often used in pharmaceutical chemistry. Such salts are also embodiments of this invention. A "pharmaceutically-acceptable (acid) addition salt" is formed from a pharmaceutically-acceptable acid as is well known in the art. Such salts include the pharmaceutically acceptable salts exemplified in Berge, S. M, Bighley, L. D., and Monkhouse, D. C., *J. Pharm. Sci.*, 66:1, (1977), which are well known to those skilled in the art.

Inorganic acids commonly employed to form such salts include hydrochloric acid, hydrobromic acid, hydroiodic acid, sulfuric acid, phosphoric acid, and the like. Organic acids commonly employed to form such salts include p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. It is well known that such compounds can form salts in various molar ratios to provide for example the hemi-acid, mono-acid, di-acid salts, etc.

The term "effective amount" means an amount of a compound of formula I which is capable of activating 5-$HT_{1F}$ receptors and/or inhibiting dural protein extravasation.

The term "suitable solvent" refers to any solvent, or mixture of solvents, inert to the ongoing reaction that sufficiently solubilizes the reactants to afford a medium within which to effect the desired reaction.

It is understood that compounds of the present invention may exist as stereoisomers. As such, all enantiomers, diastereomers, and mixtures thereof, are included within the scope of the present invention. Where specific stereochemistries are identified in this application, the Cahn-Prelog-Ingold designations of (R)- and (S)- and the cis and trans designation of relative stereochemistry are used to refer to specific isomers and relative stereochemistry. While all enantiomers, diastereomers, and mixtures thereof, are contemplated within the present invention, preferred embodiments are single enantiomers and single diastereomers.

While all of the compounds of the present invention are useful as 5-$HT_{1F}$ agonists, certain classes are preferred, as for example, compounds having any of the following enumerated selections of substituents: Compounds wherein
1) Ar is phenyl or substituted phenyl;
2) Ar is mono-, di- or tri-halo substituted phenyl;
3) Ar is heterocycle or substituted heterocycle;
4) Ar is heterocycle or substituted heterocycle wherein the heterocycle is selected from the group consisting of furanyl, thiophenyl, pyrrolyl, pyridinyl, N-methylpyrrolyl, pyrimidinyl, pyrazinyl, benzofuranyl, benzothiophenyl, indolyl;
5) Ar is heterocycle or substituted heterocycle wherein the heterocycle is selected from the group consisting of furanyl;
6) Ar is heterocycle or substituted heterocycle wherein the heterocycle is selected from the group consisting of thiophenyl;
7) Ar is heterocycle or substituted heterocycle wherein the heterocycle is selected from the group consisting of pyrrolyl;
8) Ar is heterocycle or substituted heterocycle wherein the heterocycle is selected from the group consisting of pyridinyl;
9) Ar is heterocycle or substituted heterocycle wherein the heterocycle is selected from the group consisting of N-methylpyrrolyl;
10) Ar is heterocycle or substituted heterocycle wherein the heterocycle is selected from the group consisting of pyrimidinyl;
11) Ar is heterocycle or substituted heterocycle wherein the heterocycle is selected from the group consisting of pyrazinyl;
12) Ar is heterocycle or substituted heterocycle wherein the heterocycle is selected from the group consisting of benzofuranyl;
13) Ar is heterocycle or substituted heterocycle wherein the heterocycle is selected from the group consisting of benzothiophenyl,
14) Ar is heterocycle or substituted heterocycle wherein the heterocycle is selected from the group consisting of indolyl;
15) $R^1$ is methyl;
16) $R^1$ and $R^2$ both methyl;
17) $R^3$ is hydrogen
18) $R^3$ is fluoro;
19) $R^3$ is meta or para to the amido group;
20) $R^3$ is meta to the amido group;
21) $R^3$ is fluoro and is meta to the amido group;
22) When X is —C($R^4$)=, $R^4$ is hydrogen;
23) When X is —C($R^4$)=, $R^4$ is fluoro;
24) $R^5$ is hydrogen;
25) $R^5$ is methyl;
26) Ar is substituted phenyl, $R^1$ and $R^2$ are both methyl, $R^3$ is hydrogen or fluoro, $R^4$, if present, is hydrogen, and $R^5$ is hydrogen or methyl;
27) Ar is substituted phenyl, $R^1$ and $R^2$ are both methyl, $R^3$ is hydrogen, $R^4$, if present, is fluoro, and $R^5$ is hydrogen or methyl;
28) Ar is substituted phenyl, $R^1$ and $R^2$ are both methyl, $R^3$ is hydrogen or fluoro, $R^4$, if present, is hydrogen, and $R^5$ is hydrogen;
29) Ar is substituted phenyl, $R^1$ and $R^2$ are both methyl, $R^3$ is hydrogen, $R^4$, if present, is fluoro, and $R^5$ is hydrogen;

It will be understood that the above classes may be combined to form additional preferred classes, as for example the combination of preferred selections for two or more substituents.

The compounds of the present invention may be synthesized through a number of alternative routes including those shown in Schemes 1-4. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. All substituents, unless otherwise indicated, are as previously defined, and all reagents are well known and appreciated in the art.

In one preferred synthetic route, as shown in Scheme 1, final compounds are formed by condensation of an appropriate Ar-acyl halide with an appropriate amino intermediate, II:

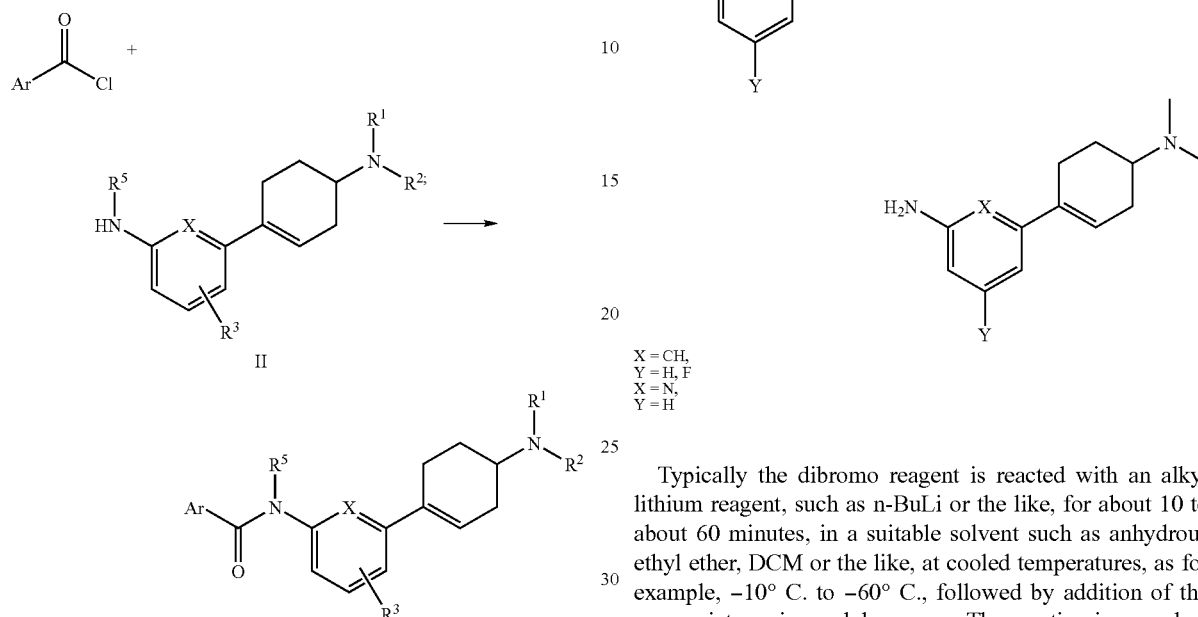

wherein the substituents are as defined above.

Typically, a mixture of the amino intermediate II, the desired $R^1$-acylhalide, a proton scavenger, such as triethylamine or pyridine, in an appropriate solvent, such as dioxane, pyridine, or the like, is heated, as for example between about 50° C. and reflux, until the reaction is complete, as for example, between about 2 and 15 hrs. It is sometimes beneficial to add a second aliquote of acyl halide and continue incubation for several hours more to provide a higher yield of final prodct. The final product is then purified by normal work-up procedures.

Amino intermediate II, can be synthesiszed according to Scheme 2, by reaction of an appropriate 1,3-dibromophenyl or 2,6-dibromopyridinyl compound with the appropriate 4-aminocyclohexanone. The amino group should be either bisubstituted with $R^1$ and $R^2$ as desired for the final product, or protected by an amino protecting group according to procedures well known in the art. If an amino protecting group is used, it can be removed in the last step to provide the desired final compound.

Scheme 2:

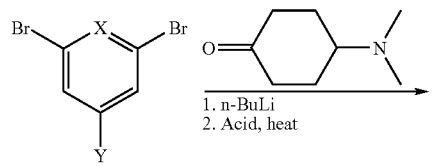

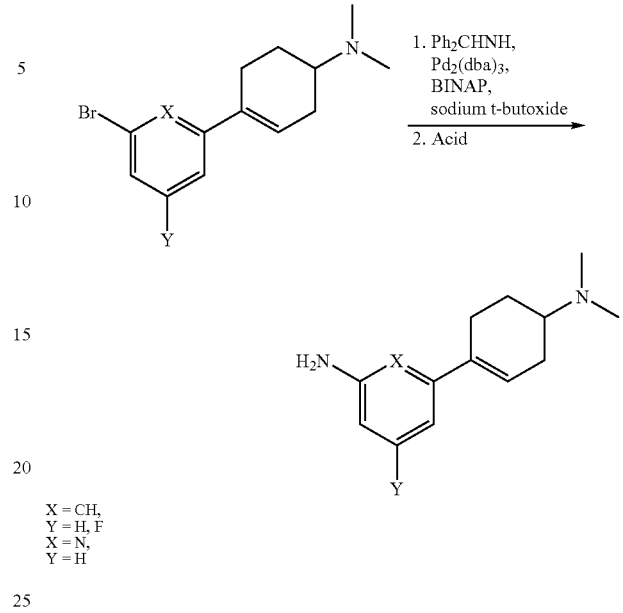

X = CH, Y = H, F
X = N, Y = H

Typically the dibromo reagent is reacted with an alkyl lithium reagent, such as n-BuLi or the like, for about 10 to about 60 minutes, in a suitable solvent such as anhydrous ethyl ether, DCM or the like, at cooled temperatures, as for example, −10° C. to −60° C., followed by addition of the appropriate aminocyclohexanone. The reaction is quenched after about 1-4 hr. with water, aqueous $NaHCO_3$ solution, or the like, followed by normal work-up procedures if desired.

The remaining bromo group is then converted to an amino group under standard conditions using benzophenone imine, tris(dibenzylideneacetone)dipalladium(0), BINAP, and sodium t-butoxide in a suitable solvent, as for example, toluene, 1,4-dioxane, or the like. Normal work-up procedures provide the amino intermediate II for compounds wherein $R^5$ is hydrogen. For compounds wherein $R^5$ is methyl or ethyl, reductive alkylation of the amino procduct in Scheme 2 with formaldehyde or acetaldehyde, respectively, provides the desired intermediate. If desired, enantiomers can be separated by known procedures, such as chiral chromatography, etc.

Compounds wherein $R^3$ is other than hydrogen can be made under similar conditions using the appropriately substituted dibromo reagent.

For compounds wherein $R^4$ is fluoro, 1-bromo-2fluoro benzene is used in the presence of a secondary amine, such as 2,2,6,6-tetramethyl-piperidine or the like, instead of a dibromo reagent. See Scheme 3.

Scheme 3

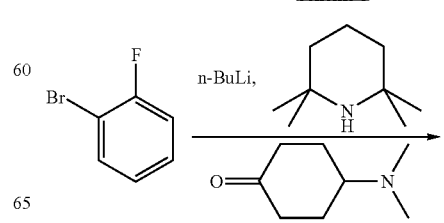

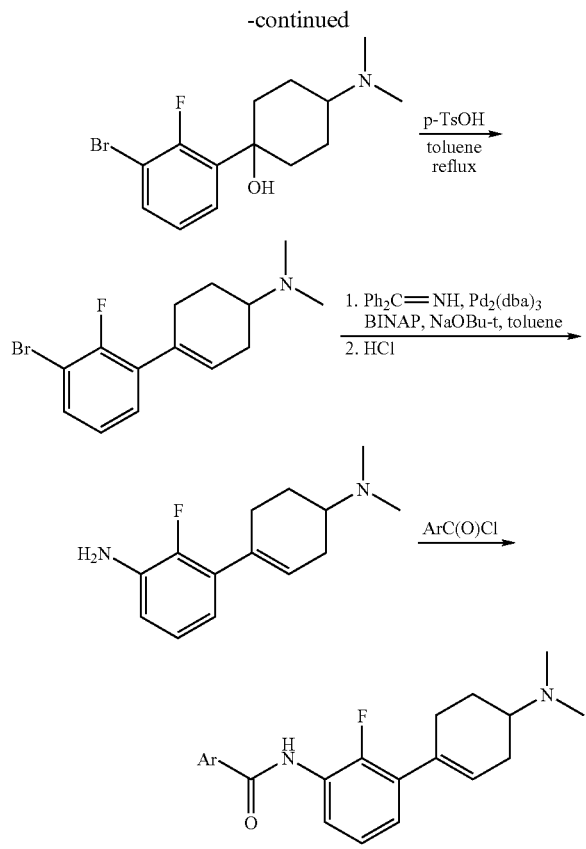
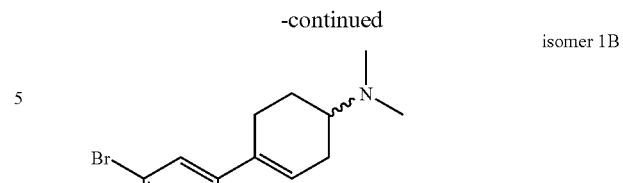

The following Preparations and Examples are provided to better elucidate the practice of the present invention and should not be interpreted in any way so as to limit the scope thereof.

PREPARATIONS

Preparation 1

(4-(3-Bromo-phenyl)-cyclohex-3-enyl)-dimethylamine

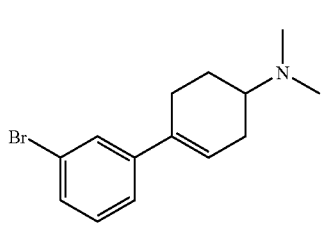
racemic

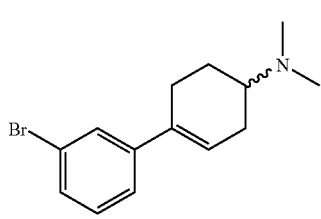
isomer 1A

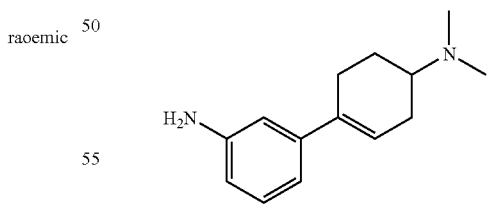
isomer 1B

Combine 1,3-dibromobenzene (6.708 g, 28.4 mmol) and anhydrous ether (90 mL) and cool to −25° C. Add n-BuLi (1.6M solution in hexanes, 19.4 mL, 3.0 mmol) to the above solution and stir for 10 min. Then add a solution of 4-dimethylamino-cyclohexanone (3.65 g, 25.8 mmol) in anhydrous ether (10 mL) through a cannula. Stir the mixture for 1.5 hr. at −10° C. and then quench with saturated NaHCO₃ solution. Separate the organic layer, extract the aqueous layer three times. Combine the organic layers, dry over sodium sulfate, filter and concentrate to give a residue. Purify the residue by chromatography (silica gel, 7% 2M NH₃/MeOH in DCM) to provide the alcohol intermediate as a mixture of two diastereomers (6.01 g).

Dissolve the above alcohol in trifluoroacetic acid (15.5 mL, 0.20 mol) and heat at 50° C. for 5 hr. Remove volatiles under reduced pressure, partition the residue in DCM/water, adjust pH>11 with 1N NaOH solution. Extract the aqueous layer three times with DCM, combine the organic layers, dry over sodium sulfate, filter and concentrate to give a residue. Purify by chromatography (silica gel, 7% 2M NH₃/MeOH in DCM) to provide the title compound (3.41 g, 47.1% two-step yield). Separate the two enantiomers by chiral HPLC (Chiralpak AD 4.6×250 mm, eluting with 0.2% dimethethylamine in acetonitrile, flow rate: 1 mL/min.) to provide two enantiomers: isomer 1A ($t_R$=13.0 min), isomer 1B ($t_R$=16.1 min), MS (ES): m/z=280.0 (m+H)⁺; ¹H NMR (CDCl₃): δ 7.54 (br, 1H), 7.38-7.29 (m, 2H), 7.22-7.16 (m, 1H), 6.10 (br, 1H), 2.55-2.41 (m, 4H), 2.37 (s, 6H), 2.27-2.13 (m, 2H), 1.58 (m, 1H).

Preparation 2

3-(4-Dimethylamino-cyclohex-1-enyl)-phenylamine (Enantiomer 1)

Combine chiral (4-(3-bromo-phenyl)-cyclohex-3-enyl)-dimethyl-amine preparation 1, isomer 1A, 1.71 g, 6.10 mmol), benzophenone imine (1.327 g, 7.32 mmol), tris(dibenzylideneacetone)dipalladium(0) (112 mg, 0.122 mmol), BINAP (228 mg, 0.366 mmol), sodium t-butoxide and toluene. Heat at 100° C. for 15 hr. Quench the reaction with 0.1N NaOH solution, extract with EtOAc three times. Combine the organic layers, dry over sodium sulfate, filter and concentrate to give a yellow residue.

Dissolve the residue in TBF (30 mL), add 5N HCl solution (3 mL), and stir for 1 hr. at room temperature. Add 0.1N HCl solution, extract with EtOAc/hexanes (1:2) twice. Keep the aqueous layer, adjust pH>11 with 5N NaOH solution, extract with DCM three times. Combine the organic layers, dry over sodium sulfate, filter and concentrate to give a residue. Purify the residue by chromatography (silica gel, 9% 2M NH$_3$/MeOH in DCM) to provide the title compound (1.048 g, 79.4%): MS (ES) 217.4 (m+H)$^+$, $^1$H NMR (CDCl$_3$) δ 7.12 (t, 1H), 6.81 (m, 1H), 6.72 (t, 1H), 6.61-6.57 (m, 1H), 6.05-6.03 (m, 1H), 3.66 (br, 2H), 2.56-2.46 (m, 3H), 2.37 (s, 6H), 2.17-2.10 (m, 3H), 1.56 (m, 1H).

Preparation 3

3-(4-Dimethylamino-Cyclohex-1-enyl)-Phenylamine (Enantiomer 2)

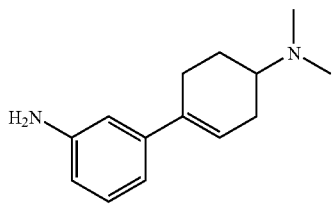

Use procedures similar to preparation 2 using chiral (4-(3-bromo-phenyl)-cyclohex-3-enyl)-dimethyl-amine (isomer 1A, preparation 1, 1.63 g, 5.82 mmol) to obtain the title compound (939 mg): MS (ES) 217.4 (M+H)$^+$.

Preparation 4

(4-(3-bromo-5-fluoro-phenyl)-cyclohex-3-enyl)-dimethyl-amine (Enantiomer 2)

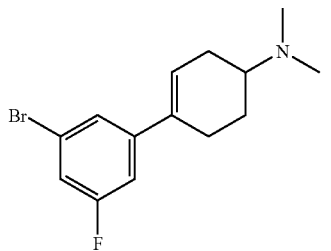

Dissolve 1,3-dibromo-5-fluoro-benzene (19.8 g, 77.90 mmol) in dry diethyl ether (300 mL) and cool to −60° C. Add 1.6M n-BuLi in hexanes (50.9 mL, 81.44 mmol) dropwise over 15 min. and stir an additional 15 min. Add a pre-cooled (−60° C.) solution of 4-dimethylamino-cyclohexanone (10.0 g, 70.8 mmol) in diethyl ether (200 mL) dropwise over 30 min. Stir at −60° C. to −20° C. for 2 hr., then warm to ambient temperature and stir for 1 hr. Quench the reaction with water (200 mL) and extract with ethyl acetate (3×200 mL). Dry over sodium sulfate, filter and concentrate. Purify the residue by flash chromatography (15% 2M NH$_3$/MeOH in DCM) to obtain 1-(3-Bromo-5-fluoro-phenyl)-4-dimethylamino-cyclohexanol as a white foam (14.5 g, 64.8%). MS (ES) m/z=316 (M−H)$^−$, 318 (M+H)$^+$; $^1$H NMR (CDCl$_3$): δ 7.41 (d, 1H, J=2 Hz), 7.15 (m, 2H), 2.3 (m, 8H), 1.78 (m, 8H).

Combine 1-(3-bromo-5-fluoro-phenyl)-4-dimethylamino-cyclohexanol (14.5 g, 45.9 mmol), p-TsOH (21.8 g, 114.6 mmol) and toluene (200 mL) and heat to reflux for 3 hr. Cool to ambient temperature and partition between ethyl acetate (500 mL) and 1M NaOH solution (250 mL). Wash the organic layer with 1M NaOH solution (200 mL) and saturated aqueous NaCl (200 mL), dry over sodium sulfate, filter and concentrate. Purify the residue by chromatography (silica gel, 10% 2M NH$_3$/MeOH in DCM) to obtain (4-(3-bromo-5-fluoro-phenyl)-cyclohex-3-enyl)-dimethyl-amine (10.8 g, 79%): MS (ES) m/z=298 (M−H)$^−$, 300 (M+H)$^+$; $^1$H NMR (CDCl$_3$): δ 7.25 (d, 1H, J=2 Hz), 7.02 (dd, 1H, J=8 Hz, J=2 Hz), 6.9 (dd, 1H, J=8 Hz, J=2 Hz), 6.04 (m, 1H), 2.38 (m, 4H), 2.27 (s, 6H), 2.09 (m, 2H), 1.48 (m, 1H).

Preparation 5

3-(4-Dimethylamino-cyclohex-1-enyl)-5-fluoro-phenylamine

Isomer 5A

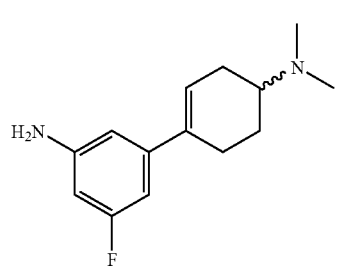

Isomer 5B

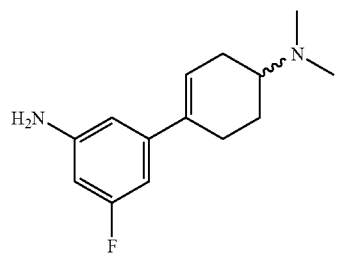

Combine (4-(3-bromo-5-fluoro-phenyl)-cyclohex-3-enyl)-dimethyl-amine (10.8 g, 36.2 mmol), benzhydrylideneamine (7.88 g, 43.5 mmol), toluene (250 mL), BINAP (0.90 g, 1.44 mmol) and sodium t-butoxide (4.87 g, 50.7 mmol) and heat to 90° C. for 10 min. until homogeneous. Add tris(dibenzylideneacetone)dipalladium(0) (0.66 g, 0.72 mmol) and heat to 100° C. for 3 hr. Add 6M HCl solution (60 mL) carefully and continue to heat at 100° C. for 1 hr. Cool to ambient temperature and wash with ethyl acetate (2×100 mL). Basify the aqueous layer with 5N NaOH solution and extract with ethyl acetate (3×250 mL). Dry the organic layer over sodium sulfate, filter and concentrate. Purify the residue by flash chromatography (silica gel, 10% 2M NH$_3$/MeOH in DCM) to obtain 3-(4-dimethylamino-cyclohex-1-enyl)-5-fluoro-phenylamine (2.84 g, 33.5%).

Resolve the enantiomers using chiral HPLC (ChiralPak AD, 4.6×250 mm, flow rate: 1 mL/min.) eluting with 100% MeOH with 0.2% dimethylethylamine to obtain nearly equal amounts of the two enantiomers: isomer 5A (t$_R$=6.0 min) and isomer 5B (t$_R$=7.1 min). Spectra for both compounds: MS (ES) m/z=235 (M+H)$^+$; $^1$H NMR (CDCl$_3$): δ 6.45 (m, 2H), 6.24 (dd, 1H, J=8 Hz, J=2 Hz), 6.03 (m, 1H), 3.75 (bs, 2H), 2.4 (m, 4H), 2.35 (s, 6H), 2.12 (m, 2H), 1.52 (m, 1H).

Preparation 6

1-(3-Bromo-2-fluoro-phenyl)-4-dimethylamino-cyclohexanol

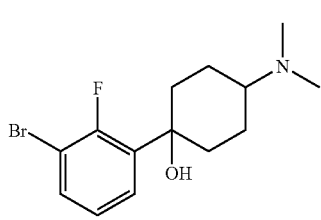

Add n-BuLi (20.2 mL, 1.6M in hexanes, 32.3 mmol) into a solution of 2,2,6,6-tetramethyl-piperidine (4.56 g, 32.6 mmol) in hexanes (30 mL) at −78° C. Add 1-bromo-2-fluoro-benzene (4.71 g, 26.9 mmol) and stir for 1 hr. Slowly add 4-dimethylamino-cyclohexanone (3.80 mL) in hexanes (30 mL) and stir for 1 hr. Remove the cooling bath and stir for two more hours. Partition the reaction mixture between saturated aqueous NaCl and ethyl acetate, dry the organic phase with anhydrous sodium sulfate, evaporate the solvent, and purify the residue by chromatography on a silica gel column (DCM: 2M $NH_3$ in MeOH, gradient) to give the title compound (2.04 g): MS (ES): m/z=318 $(M+H)^+$ and 316 $(M-H)^-$. $^1$HNMR ($CDCl_3$): δ 7.43 (m, 2H), 6.98 (m, 1H), 2.45 (m, 2H), 2.21 (s, 6H), 2.13 (m, 1H), 1.92 (m, 2H), 1.64 (m, 4H).

Preparation 7

(4-(3-Bromo-2-fluoro-phenyl)-cyclohex-3-enyl)-dimethyl-amine

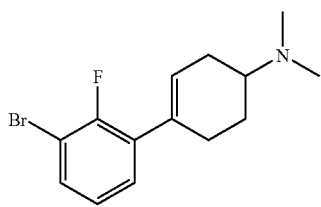

Heat 1-(3-bromo-2-fluoro-phenyl)-4-dimethylamino-cyclohexanol (preparation 6, 2.04 g, 6.45 mmol) and p-TsOH monohydrate (3.07 g, 16 mmol) in toluene (50 mL) at reflux for 2 hr. Partition the reaction mixture between saturated aqueous NaCl and ethyl acetate, dry the organic phase with anhydrous sodium sulfate, evaporate the solvent, and purify the residue by chromatography on a silica gel column (DCM: 2M $NH_3$ in MeOH, gradient) to give the title product (1.70 g): MS (ES): m/z=300 $(M+H)^+$ and 298 $(M-H)^-$. $^1$HNMR ($CDCl_3$): δ 7.39 (m, 1H), 7.14 (m, 1H), 6.94 (m, 1H), 5.88 (m, 1H), 2.60-2.38 (m, 4H), 2.35 (s, 6H), 2.20 (m, 1H), 2.08 (m, 1H), 1.56 (m, 1H).

Preparation 8

3-(4-Dimethylamino-cyclohex-1-enyl)-2-fluoro-phenylamine

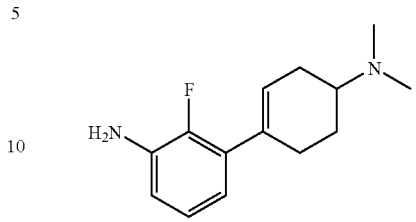

Combine (4-(3-bromo-2-fluoro-phenyl)-cyclohex-3-enyl)-dimethyl-amine (preparation 7, 1.70 g, 6.84 mmol), benzophenone imine (1.24 g, 6.84 mmol), tris(dibenzylideneacetone)dipalladium(0) (0.104 g, 0.11 mmol), racemic BINAP (0.142 g, 0.228 mmol), and sodium t-butoxide (0.767 g, 0.8 mmol) with toluene (5 mL) and heat at reflux for 2 hr. Dissolve the reaction mixture in MeOH and filter through a SCX column (Bond Elut™, 10 g), wash with MeOH, elute the product with 2M $NH_3$ in MeOH, evaporate the solvent, and further purify on a silica gel column (DCM:2M $NH_3$ in MeOH, gradient) to give pure benzhydrylidene-(3-(4-dimethylamino-cyclohex-1-enyl)-2-fluoro-phenyl)-amine (2.39 g): MS (ES): m/z=399 $(M+H)^+$. $^1$H NMR ($CDCl_3$): δ 7.76 (m, 2H), 7.46 (m, 1H), 7.40 (m, 2H), 7.25 (m, 4H), 7.13 (m, 2H), 6.85 (m, 1H), 6.73 (m, 1H), 6.65 (m, 1H), 5.70 (m, 1H), 3.05 (m, 1H), 2.61 (s, 6H), 2.6-2.2 (m, 5H), 1.75 (m, 1H).

Add concentrated hydrochloric acid (2 mL) into a solution of the above benzhydrylidene-(3-(4-dimethylamino-cyclohex-1-enyl)-2-fluoro-phenyl)-amine (2.27 g, 5.7 mmol) in THF (20 mL) and heat at reflux for 1 hr. Basify the reaction mixture with conc. $NH_4OH$ and partition between saturated aqueous NaCl and DCM, dry the organic phase with anhydrous sodium sulfate, evaporate the solvent, and purify the residue by chromatography on a silica gel column (DCM: 2M $NH_3$ in MeOH, gradient) to give the title compound (1.189 g): MS (ES): m/z=235 $(M+H)^+$. $^1$H NMR ($CDCl_3$): δ 6.85 (m, 1H), 6.64 (m, 1H), 6.87 (m, 1H), 5.87 (m, 1H), 3.70 (br s, 2H), 2.3-2.6 (m, 4H), 2.35 (s, 6H), 2.18 (m, 1H), 2.06 (m, 1H), 1.55 (m, 1H).

Preparation 9

(4-(6-Bromo-pyridin-2-yl)-cyclohex-3-enyl)-dimethyl-amine

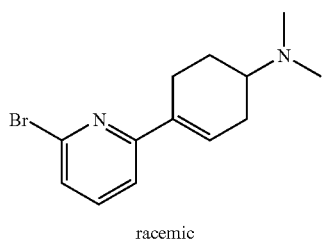

racemic

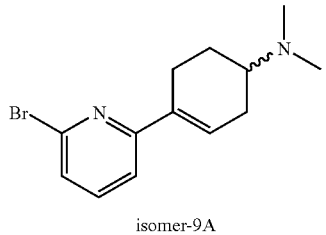

isomer-9A

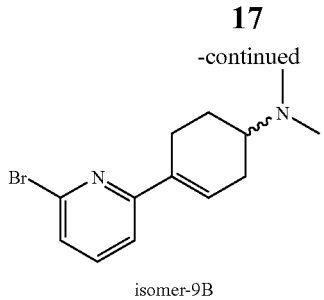

isomer-9B

Under a nitrogen atmosphere, dissolve 2,6-dibromopyridine (10 g, 42.4 mmol) in anhydrous DCM (250 mL). Cool to −78° C. Add a solution of n-BuLi (1.6 M in hexanes) (29 mL, 46.2 mmol) very slowly via a syringe. After the addition, stir the reaction at −78° C. for 1 hr. Add a solution of 4-dimethylamino-cyclohexanone (5.4 g, 38.5 mmol) in anhydrous DCM (10 mL) dropwise to the reaction mixture via a syringe. Stir the reaction at −78° C. for 90 min. then allow to slowly warm to room temperature over 4 hr. Quench the reaction with saturated NaHCO$_3$ solution. Dilute with more DCM, wash with more saturated NaHCO$_3$ solution. Separate the organic layer, dry over anhydrous sodium sulfate, then evaporate the solvent under reduced pressure. Purify the residue by chromatography (silica gel, 6% 2M NH$_3$-MeOH in DCM) to yield the desired 1-(6-bromo-pyridin-2-yl)-4-dimethylamino-cyclohexanol as a mixture of diastereomers (7.7 g, 67% yield): MS (ES): m/z=299 (M+H)$^+$.

Mix the above 1-(6-bromo-pyridin-2-yl)-4-dimethylamino-cyclohexanol (7 g, 23.4 mmol), p-toluenesulfonic acic monohydrate (15.3 g, 80.5 mmol), anhydrous toluene (600 mL). Heat at reflux for 16 hr. with a Dean Stark trap. Cool down to room temperature. Concentrate under reduced pressure. Partition between ethyl acetate and a 2M NaOH solution. Separate the organic layer, extract the aqueous layer twice with ethyl acetate. Combine the organic fractions, dry over sodium sulfate and concentrate to a residue. Purify the residue by chromatography (silica gel, 6% 2M NH$_3$-MeOH in DCM) to yield (4-(6-bromo-pyridin-2-yl)-cyclohex-3-enyl)-dimethyl-amine (5.3 g, 81% yield): MS (ES): m/z=299 (M+H)$^+$; $^1$H NMR (CDCl$_3$): δ 7.45 (m, 1H), 7.27 (m, 2H), 6.72 (m, 1H), 2.69 (m, 1H), 2.45 (m, 3H), 2.33 (s, 6H), 2.21 (m, 2H), 1.58 (m, 1H).

Chiral HPLC resolution (Chiralpak AD 4.6×250 mm, 5% MeOH in acetonitrile, flow rate: 1 mL/min.) of the racemic mixture provides two enantiomers of the title compound: isomer-9A (1.47 g) (t$_R$=9.2 min) and isomer-9B (1.49 g) (t$_R$=13.7 min).

Preparation 10

6-(4-Dimethylamino-cyclohex-1-enyl)-pyridin-2-ylamine (Enantiomer 1)

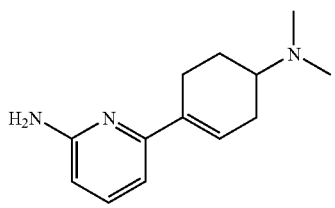

Use procedures similar to preparation 2 using (4-(6-bromo-pyridin-2-yl)-cyclohex-3-enyl)-dimethylamine (isomer 9A, preparation 9, 1.35 g, 4.80 mmol) to provide the title compound as a slightly yellow oil (912 mg, 80% yield): MS (ES): m/z=218.0 (M+H)$^+$; $^1$H NMR (CDCl$_3$): δ 7.38 (1H), 6.70 (d, 1H), 6.62 (m, 1H), 6.36 (d, 1H), 4.42 (br, 2H), 2.67 (m, 1H), 2.43 (m, 3H), 2.33 (s, 6H), 2.11 (m, 2H), 1.53 (m, 1H).

Preparation 11

6-(4-Dimethylamino-cyclohex-1-enyl)-pyridin-2-ylamine (Enantiomer 2)

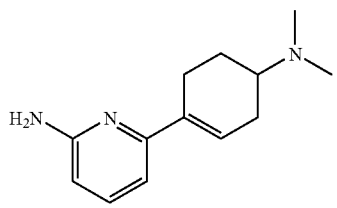

Use procedures similar to preparation 2 using (4-(6-bromo-pyridin-2-yl)-cyclohex-3-enyl)-dimethylamine (isomer 9B, preparation 9, 1.49 g, 5.30 mmol) to provide the title compound as a slightly yellow oil (711 mg, 62% yield): MS (ES): m/z=218.0 (m+H)$^+$.

EXAMPLES

Example 1

N-(3-(4-Dimethylamino-cyclohex-1-enyl)-phenyl)-4-fluoro-benzamide hydrochloride salt

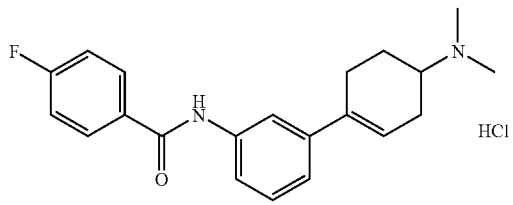

Add 4-fluorobenzoyl chloride (155 mg, 0.976 mmol) to a solution of 3-(4-dimethylamino-cyclohex-1-enyl)-phenylamine (preparation 2, 176 mg, 0.814 mmol) in pyridine (8 mL) and heat at 55° C. overnight. Remove the volatile under reduced pressure, dissolve the residue in DCM, wash with 0.1N NaOH, dry over sodium sulfate, filter and concentrate to give a residue. Purify the residue by chromatography (silica gel, 8% 2M NH$_3$/MeOH in DCM) to provide the free base of the title compound (203 mg, 74%): MS (ES): m/z=339.2 (M+H)$^+$; $^1$H NMR (CDCl$_3$): δ 7.92 (m, 3H), 7.70 (s, 1H), 7.52 (d, 1H), 7.32 (t, 1H), 7.18 (m, 3H), 6.12 (m, 1H), 2.50 (m, 4H), 2.37 (s, 6H), 2.13 (m, 2H), 1.57 (m, 1H).

Dissolve the free base in MeOH, add 0.6 mL 1N HCl in ether, stir the mixture, add more ether to precipitate the title compound. Remove most of the supernatant with pipette, dry the product under a nitrogen stream.

Example 2

N-(3-(4-Dimethylamino-cyclohex-1-enyl)-phenyl)-2,4,6-trifluoro-benzamide hydrochloride salt

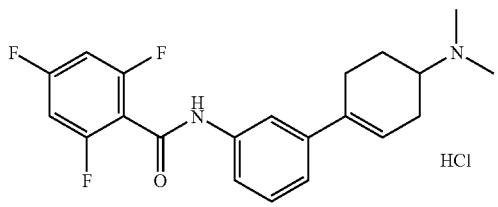

Using a method similar to example 1, using 2,4,6-trifluorobenzoyl chloride (127 mg, 0.655 mmol) and 3-(4-dimethylamino-cyclohex-1-enyl)-phenylamine (preparation 2, 118 mg, 0.545 mmol) provides the title compound (free base, 180 mg, 88%). Free base: MS (ES): m/z=375.2 (M+H)$^+$; $^1$H NMR (CDCl$_3$): δ 7.78 (s, br, 1H), 7.67 (s, 1H), 7.48 (d, 1H), 7.32 (t, 1H), 7.22 (d, 1H), 6.78 (m, 2H), 6.12 (m, 1H), 2.50 (m, 4H), 2.37 (s, 6H), 2.15 (m, 2H), 1.57 (m, 1H). Hydrochloride salt: Anal. cal'd for C$_{21}$H$_{21}$F$_3$N$_2$O.HCl.H$_2$O: C, 58.81; H, 5.64; N, 6.53. Found: C, 58.95; H, 5.30; N, 6.55.

Example 3

3-Chloro-N-(3-(4-Dimethylamino-cyclohex-1-enyl)-phenyl)-2,6-difluoro-benzamide hydrochloride salt

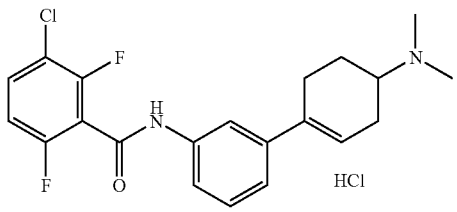

Using a method similar to example 1, using 3-chloro-2,6-difluorobenzoyl chloride (142 mg, 0.67 mmol) and 3-(4-dimethylamino-cyclohex-1-enyl)-phenylamine (preparation 2, 121 mg, 0.56 mmol) provides the title compound (free base 166 mg, 76%). Free base: MS (ES): m/z=391.2 (M+H)$^+$; $^1$H NMR (CDCl$_3$): δ 7.79 (s, br, 1H), 7.68 (br, 1H), 7.49 (m, 2H), 7.34 (t, 1H), 7.22 (d, 1H), 7.00 (dt, 1H), 6.12 (m, 1H), 2.46 (m, 4H), 2.38 (s, 6H), 2.15 (m, 2H), 1.59 (m, 1H). Hydrochloride salt: Anal. cal'd for C$_{21}$H$_{21}$ClF$_2$N$_2$O.HCl 0.25H$_2$O: C, 58.41; H, 5.25; N, 6.49. Found: C, 58.65; H, 5.16; N, 6.51.

Example 4

2-Chloro-N-(3-(4-Dimethylamino-cyclohex-1-enyl)-phenyl)-6-fluoro-benzamide hydrochloride salt

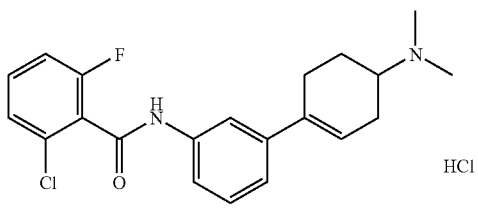

Using a method similar to example 1, using 2-chloro-6-fluorobenzoyl chloride (132 mg, 0.69 mmol) and 3-(4-dimethylamino-cyclohex-1-enyl)-phenylamine (preparation 2, 124 mg, 0.57 mmol) provides the title compound (free base 208 mg, 98%). Free base: MS (ES): m/z=373.2 (M+H)$^+$; $^1$H NMR (CDCl$_3$): δ 7.68 (m, 2H), 7.52 (d, 1H), 7.36 (m, 2H), 7.25 (m, 1H), 7.23 (t, 1H), 7.10 (m, 1H), 6.12 (m, 1H), 2.50 (m, 4H), 2.36 (s, 6H), 2.15 (m, 2H), 1.58 (m, 1H). Hydrochloride salt: Anal. cal'd for C$_{21}$H$_{22}$ClFN$_2$O.HCl 0.6H$_2$O: C, 60.03; H, 5.81; N, 6.67. Found: C, 59.75; H, 5.31; N, 6.55.

Example 5

2-Chloro-N-(3-(4-Dimethylamino-cyclohex-1-enyl)-phenyl)-4-fluoro-benzamide hydrochloride salt

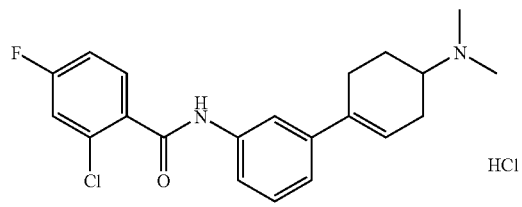

Using a method similar to example 1, using 2-chloro-4-fluorobenzoyl chloride (128 mg, 0.66 mmol) and 3-(4-dimethylamino-cyclohex-1-enyl)-phenylamine (preparation 2, 119 mg, 0.55 mmol) provides the title compound (free base 187 mg, 91%). Free base: MS (ES): m/z=373.2 (M+H)$^+$; $^1$H NMR (CDCl$_3$): δ 8.08 (s, br, 1H), 7.77 (m, 1H), 7.68 (s, br, 1H), 7.52 (d, 1H), 7.32 (t, 1H), 7.19 (m, 2H), 7.09 (m, 1H), 6.11 (m, 1H), 2.51 (m, 4H), 2.36 (s, 6H), 2.14 (m, 2H), 1.57 (m, 1H). Hydrochloride salt: Anal. cal'd for C$_{21}$H$_{22}$ClFN$_2$O.HCl.0.5H$_2$O: C, 60.29; H, 5.78; N, 6.70. Found: C, 60.17; H, 5.45; N, 6.65.

Example 6

N-(3-(4-Dimethylamino-cyclohex-1-enyl)-phenyl)-4-fluoro-benzamide Hydrochloride Salt

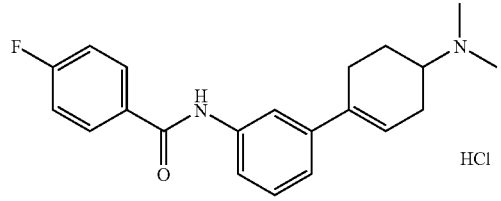

Use a method similar to example 1, use 3-(4-dimethylamino-cyclohex-1-enyl)-phenylamine (enantiomer 2, preparation 3, 169 mg, 0.78 mmol) and 4-fluorobenzoyl chloride (149 mg, 0.94 mmol) to provide 89 mg (34%) of the free base of the title compound: MS (ES): m/z=339.2 (M+H)$^+$; $^1$H NMR (CDCl$_3$): δ 7.91 (m, 3H), 7.69 (br, 1H), 7.50 (d, 1H), 7.33 (t, 1H), 7.18 (m, 3H), 6.13 (m, 1H), 2.51 (m, 4H), 2.37 (s, 6H), 2.13 (m, 2H), 1.57 (m, 1H). Hydrochloride salt: Anal. cal'd for C$_{21}$H$_{23}$FN$_2$O.HCl.0.5H$_2$O: C, 65.70; H, 6.56; N, 7.30. Found: C, 65.30; H, 6.16; N, 7.21.

Example 7

N-(3-(4-Dimethylamino-cyclohex-1-enyl)-phenyl)-2,4,6-trifluoro-benzamide Hydrochloride Salt

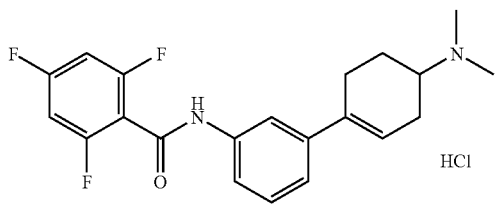

Using a method similar to example 1, using 2,4,6-trifluorobenzoyl chloride (105 mg, 0.54 mmol) and chiral 3-(4-dimethylamino-cyclohex-1-enyl)-phenylamine (enantiomer 2, preparation 3, 97 mg, 0.45 mmol) provides of the free base of the title compound (free base 142 mg, 85%): Free base: MS (ES): m/z=375.2 (M+H)$^+$; $^1$H NMR (CDCl$_3$): δ 7.80 (s, br, 1H), 7.66 (t, 1H), 7.48 (d, 1H), 7.32 (t, 1H), 7.21 (dt, 1H), 6.78 (m 2H), 6.12 (m, 1H), 2.54 (m, 4H), 2.37 (s, 6H), 2.14 (m, 2H), 1.57 (m, 1H). Hydrochloride salt: Anal. cal'd for C$_{21}$H$_{21}$F$_3$N$_2$O.HCl.1.2H$_2$O: C, 58.32; H, 5.69; N, 6.48. Found: C, 58.21; H, 5.03; N, 6.39.

Example 8

2-Chloro-N-(3-(4-dimethylamino-cyclohex-1-enyl)-phenyl)-6-fluoro-benzamide hydrochloride salt

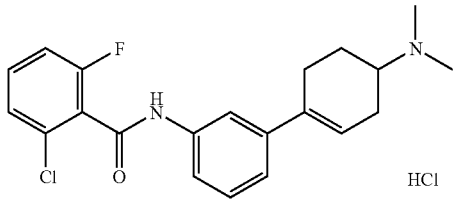

Using a method similar to example 1, using 2-chloro-6-fluorobenzoyl chloride (103 mg, 0.53 mmol) and 3-(4-dimethylamino-cyclohex-1-enyl)-phenylamine (enantiomer 2, preparation 3, 96 mg, 0.44 mmol) provides the title compound (free base 150 mg, 91%): Free base: MS (ES): m/z=373.1 (M+H)$^+$; $^1$H NMR (CDCl$_3$): δ7.90 (s, 1H), 7.67 (t, 1H), 7.52 (d, 1H), 7.27 (m, 1H), 7.08 (m, 1H), 6.10 (m, 1H), 2.52 (m, 4H), 2.34 (s, 6H), 2.12 (m, 2H), 1.55 (m, 1H). Hydrochloride salt: Anal. cal'd for C$_{21}$H$_{22}$ClFN$_2$O.HCl0.25H$_2$O: C, 60.95; H, 5.72; N, 6.77. Found: C, 60.81; H, 5.57; N, 6.81.

Example 9

2-Chloro-N-(3-(4-dimethylamino-cyclohex-1-enyl)-phenyl)-4-fluoro-benzamide hydrochloride salt

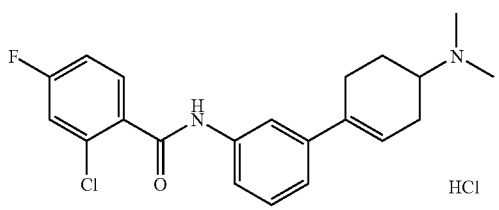

Using a method similar to example 1, using 2-chloro-4-fluorobenzoyl chloride (106 mg, 0.55 mmol) and 3-(4-dimethylamino-cyclohex-1-enyl)-phenylamine (enantiomer 2, preparation 3, 99 mg, 0.46 mmol) provides the title compound (free base 162 mg, 94%): MS (ES): m/z=373.2 (M+H)$^+$; $^1$H NMR (CDCl$_3$): δ 8.04 (s, br, 1H), 7.78 (m, 1H), 7.68 (s, 1H), 7.50 (d, 1H), 7.33 (t, 1H), 7.20 (m, 2H), 7.10 (m, 1H), 6.12 (m, 1H), 2.55 (4H), 2.37 (s, 6H), 2.15 (m, 2H), 1.57 (m, 1H). Hydrochloride salt: Anal. cal'd for C$_{21}$H$_{22}$ClFN$_2$O.HCl 0.5H$_2$O: C, 60.29; H, 5.78; N, 6.70. Found: C, 60.11; H, 5.42; N, 6.62.

Example 10

2-Chloro-N-(3-(4-dimethylamino-cyclohex-1-enyl)-5-fluoro-phenyl)-4-fluoro-benzamide hydrochloride salt

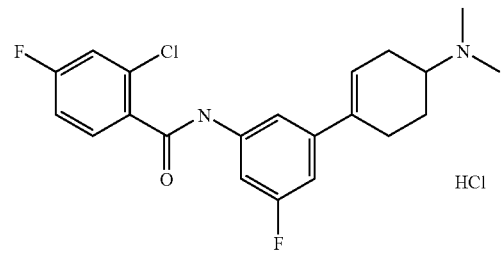

Combine chiral 3-(4-dimethylamino-cyclohex-1-enyl)-5-fluoro-phenylamine (isomer 5A, preparation 5, 0.25 g, 1.07 mmol), 2-chloro-4-fluoro-benzoyl chloride (0.31 g, 1.6 mmol) and 1,4-dioxane (5 mL) and heat to reflux for 3 hr. Cool to ambient temperature and remove volatiles. Purify the residue by flash chromatography (silica gel, 10% 2M NH$_3$/MeOH in DCM) to obtain the free base of the title compound (0.34 g, 81%). Convert to the hydrochloride salt by dissolving in ether and treating with 1M HCl in ether: MS (ES) m/z=391 (M+H)$^+$; $^1$H NMR of free base (CDCl$_3$): δ 8.19 (s, 1H), 7.72 (m, 1H), 7.42 (d, 1H, J=10 Hz), 7.26 (s, 1H), 7.16 (m, 1H), 7.06 (m, 1H), 6.86 (d, 1H, J=10 Hz), 6.09 (bs, 1H), 2.40 (m, 4H), 2.32 (s, 6H), 2.11 (m, 2H), 1.53 (m, 1H).

Example 11

N-(3-(4-Dimethylamino-cyclohex-1-enyl)-5-fluoro-phenyl)-2,4,6-trifluoro-benzamide hydrochloride salt

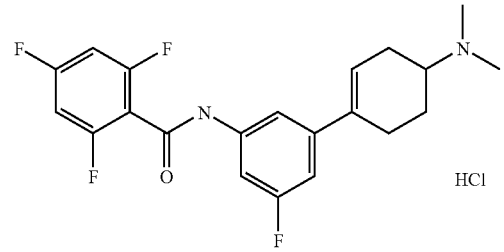

Using a method similar to example 10, using 2,4,6-trifluoro-benzoyl chloride and 3-(4-dimethylamino-cyclohex-1-enyl)-5-fluoro-phenylamine (isomer 5A, preparation 5) provides the title compound: Free base MS (ES) m/z=393 (M+H)$^+$; $^1$H NMR of free base (CDCl$_3$): δ 7.68 (s, 1H), 7.42 (d, 1H, J=10 Hz), 7.28 (s, 1H), 6.91 (dd, 1H, J=10 Hz, J=2 Hz), 6.77 (dd, 2H, J=10 Hz, J=10 Hz), 6.11 (bs, 1H), 2.43 (m, 4H), 2.35 (s, 6H), 2.16 (m, 2H), 1.58 (m, 1H).

Example 12

2-Chloro-N-(3-(4-dimethylamino-cyclohex-1-enyl)-5-fluoro-phenyl)-4-fluoro-benzamide hydrochloride salt

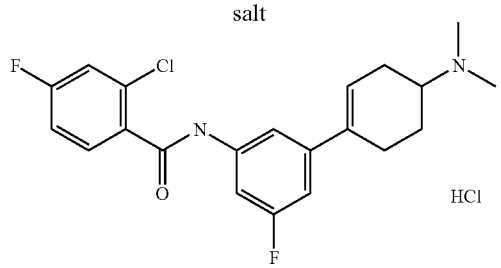

Using a method similar to example 10, using 2-chloro-4-fluorobenzoyl chloride and amine isomer 5B (preparation 5) provides the title compound: MS (ES) m/z=391 (M+H)$^+$; $^1$H NMR of free base (CDCl$_3$): δ 8.19 (s, 1H), 7.72 (m, 1H), 7.42 (d, 1H, J=10 Hz), 7.26 (s, 1H), 7.16 (m, 1H), 7.06 (m, 1H), 6.86 (d, 1H, J=10 Hz), 6.09 (bs, 1H), 2.40 (m, 4H), 2.32 (s, 6H), 2.11 (m, 2H), 1.53 (m, 1H).

Example 13

N-(3-(4-Dimethylamino-cyclohex-1-enyl)-5-fluoro-phenyl)-2,4,6-trifluoro-benzamide hydrochloride salt

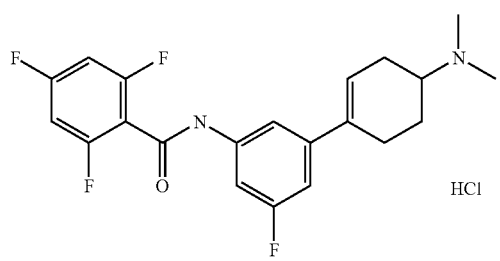

Using a method similar to example 10, using 2,4,6-trifluorobenzoyl chloride and amine isomer 5B (preparation 5) provides the title compound: MS (ES) m/z=393 (M+H)$^+$; $^1$H NMR of free base (CDCl$_3$): δ 7.68(s, 1H), 7.42(d, 1H, J=10 Hz), 7.28 (s, 1H), 6.91 (dd, 1H, J=10 Hz, J=2 Hz), 6.77 (dd, 2H, J=10 Hz, J=10 Hz), 6.11 (bs, 1H), 2.43 (m, 4H), 2.35 (s, 6H), 2.16 (m, 2H), 1.58 (m, 1H).

Example 14

N-(3-(4-Dimethylamino-cyclohex-1-enyl)-2-fluoro-phenyl)-4-fluoro-benzamide hydrochloride salt

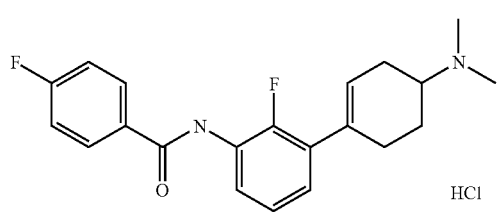

Reflux a mixture of 3-(4-dimethylamino-cyclohex-1-enyl)-2-fluoro-phenylamine (preparation 8, 0.115 g, 0.49 mmol) and 4-fluoro-benzoyl chloride (93 mg, 0.586 mmol) in dioxane (20 mL) for 2 hrs. Filter the reaction mixture through a SCX column (Bond Elut™, 10 g), wash with MeOH, elute the product with 2M NH$_3$ in MeOH, evaporate the solvent, and further purify on a silica gel column (DCM:2M NH$_3$ in MeOH, gradient) to give the free base of the title compound (0.125 g, 72%): MS (ES): m/z=357 (M+H)$^+$. $^1$H NMR (CDCl$_3$): δ 8.30 (m, 1H), 8.00 (m, 1H), 7.91 (m, 2H), 7.18 (m, 2H), 7.12 (m, 1H), 6.99 (m, 1H), 5.90 (m, 1H), 2.68 (m, 1H), 2.50 (m, 3H), 2.43 (s, 6H), 2.26 (m, 1H), 2.15 (m, 1H), 1.64 (m, 1H).

Dissolve N-(3-(4-dimethylamino-cyclohex-1-enyl)-2-fluoro-phenyl)-4-fluoro-benzamide (0.115 g) in DCM, add 1N HCl in ethyl ether (0.35 mL), evaporate to give the title compound.

Example 15

N-(3-(4-Dimethylamino-cyclohex-1-enyl)-2-fluoro-phenyl)-2,4,6-trifluoro-benzamide hydrochloride salt

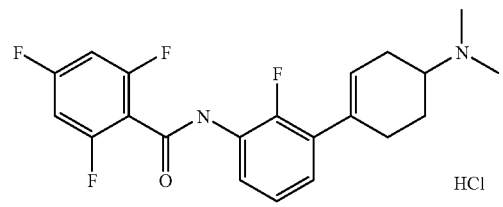

Using a method similar to example 14, using 2,4,6-trifluorobenzoyl chloride provides the title compound: MS (ES): m/z 357 (M+H)$^+$; $^1$H NMR of the free base (CDCl$_3$): δ 8.28 (m, 1H), 7.90 (br s, 1H), 7.10 (m, 1H), 7.01 (m, 1H), 6.75 (m, 2H), 5.89 (m, 1H), 2.35-2.60 (m, 4H), 2.36 (s, 6H), 2.20 (m, 1H), 2.08 (m, 1H), 1.58 (m, 1H).

Example 16

2-Chloro-N-(3-(4-dimethylamino-cyclohex-1-enyl)-2-fluoro-phenyl)-4-fluoro-benzamide hydrochloride salt

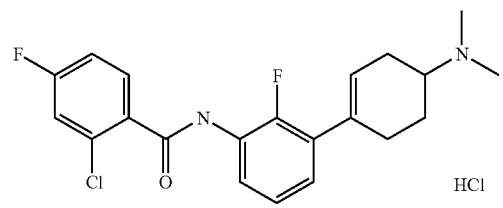

Using a method similar to example 14, using 2-chloro-4-fluorobenzoyl chloride provides the title compound: MS (ES): m/z 391 (M+H)$^+$; $^1$H NMR of the free base (CDCl$_3$): 8.30 (m, 2H), 7.86 (m, 1H), 7.21 (m, 1H), 7.12 (m, 2H), 7.00 (m, 1H), 5.90 (m, 1H), 2.35-2.60 (m, 4H), 2.37 (s, 6H), 2.21 (m, 1H), 2.10 (m, 1H), 1.59 (m, 1H).

Example 17

2-Chloro-N-(3-(4-dimethylamino-cyclohex-1-enyl)-2-fluoro-phenyl)-6-fluoro-benzamide hydrochloride salt

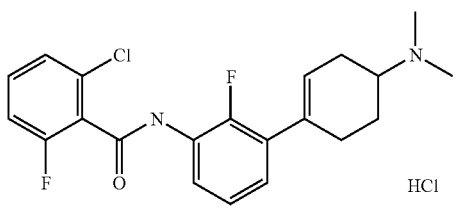

Using a method similar to example 14, using 2-chloro-6-fluorobenzoyl chloride provides the title compound: MS (ES): m/z 391 (M+H)$^+$; $^1$H NMR of the free base (CDCl$_3$): δ 8.31 (m, 1H), 7.76 (br s, 1H), 7.35 (m, 1H), 7.26 (m, 1H), 7.12 (m, 2H), 7.02 (m, 1H), 5.89 (m, 1H), 2.35-2.60 (m, 4H), 2.36 (s, 6H), 2.21 (m, 1H), 2.10 (m, 1H), 1.58 (m, 1H).

Example 18

2,4,6-Trichloro-N-(3-(4-dimethylamino-cyclohex-1-enyl)-2-fluoro-phenyl)-benzamide hydrochloride salt

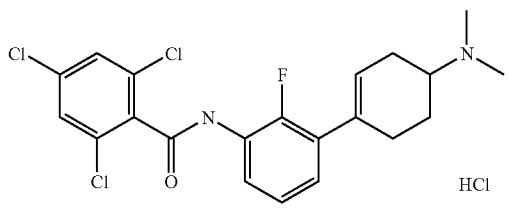

Using a method similar to example 14, using 2,4,6-trichlorobenzoyl chloride provides the title compound: MS (ES): m/z 441 (M), 443 (M+2); $^1$H NMR of the free base (CDCl$_3$): δ 8.28 (m, 1H), 7.64 (br s, 1H), 7.40 (s, 2H), 7.13 (m, 1H), 7.03 (m, 1H), 5.89 (m, 1H), 2.35-2.63 (m, 4H), 2.38 (s, 6H), 2.22 (m, 1H), 2.10 (m, 1H), 1.59 (m, 1H).

Example 19

N-(6-(4-Dimethylamino-cyclohex-1-enyl)-pyridin-2-yl)-2,4,6-trifluoro-benzamide di-hydrochloride salt isomer 1

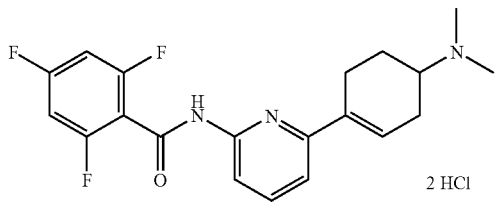

Add 2,4,6-trifluorobenzoyl chloride (117 mg, 0.60 mmol) to a solution of 6-(4-dimethylamino-cyclohex-1-enyl)-pyridin-2-ylamine, isomer 1 (preparation 10, 100 mg, 0.46 mmol) in pyridine (6 mL) and heat at 55° C. overnight. Re-add another portion of 2,4,6-trifluorobenzoyl chloride (50 mg, 0.26 mmol) and heat at 65° C. for 4 hr. Remove volatiles under reduced pressure, dissolve the residue in 1N HCl, extract twice with ethyl ether. Adjust aqueous layer to pH>11 with 5N NaOH. Extract the aqueous layer there times with DCM. Combine organic layers, dry over sodium sulfate, filter and concentrate to give a residue. Purify the residue by chromatography (silica gel, 5% 2M NH$_3$/MeOH in DCM) to provide the free amine of the title compound as a colorless oil (84 mg, 49%): MS (ion spray): m/z=376.2 (M+H)$^+$; $^1$H NMR (CDCl$_3$): δ 8.91 (s, br, 1H), 8.20 (d, 1H), 7.73 (t, 1H), 7.14 (d, 1H), 6.71 (m, 2H), 6.61 (m, 1H), 2.65 (m, 1H), 2.44 (m, 3H), 2.35 (s, 6H), 2.12 (m, 2H), 1.53 (m, 1H). Using a salt formation method similar to that in example 1 provides the di-hydrochloride salt. Di-hydrochloride salt: Anal. cal'd for C$_{20}$H$_{20}$F$_3$N$_3$O.2HCl: C, 53.58; H, 4.95; N, 9.37. Found: C, 53.42; H, 4.91; N, 9.23.

Example 20

2-Chloro-N-(6-(4-Dimethylamino-cyclohex-1-enyl)-pyridin-2-yl)-4-fluoro-benzamide di-hydrochloride salt, isomer 1

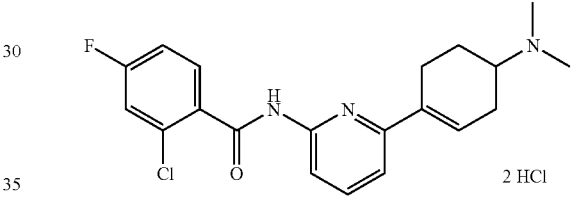

Using a method similar to example 1, using 2-chloro-4-fluoro-benzoyl chloride (116 mg, 0.60 mmol) and 6-(4-dimethylamino-cyclohex-1-enyl)-pyridin-2-ylamine, isomer 1 (preparation 10, 100 mg, 0.46 mmol) provides of the title compound as a colorless oil (135 mg, 78%): MS (ES): m/z=374.1 (M+H)$^+$; $^1$HNMR (CDCl$_3$): δ 8.80 (s, br, 1H), 8.19 (d, 1H), 7.69 (m, 2H), 7.18 (m, 2H), 7.05 (m, 1H), 6.64 (m, 1H), 2.70 (m, 1H), 2.46 (m, 3H), 2.36 (s, 6H), 2.16 (m, 2H), 1.54 (m, 1H). Di-hydrochloride salt: Anal. cal'd for C$_{20}$H$_{21}$ClFN$_3$O.2HCl: C, 53.77; H, 5.19; N, 9.41. Found: C, 54.13; H, 5.34; N, 9.41.

Example 21

2-Chloro-N-(6-(4-Dimethylamino-cyclohex-1-enyl)-pyridin-2-yl)-6-fluoro-benzamide di-hydrochloride salt, isomer 1

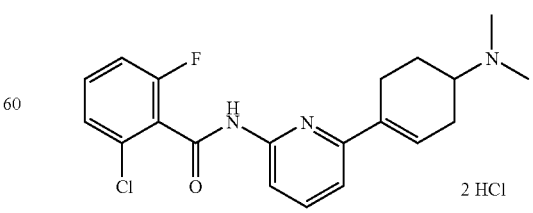

Using a method similar to example 1, using 2-chloro-6-fluoro-benzoyl chloride (116 mg, 0.60 mmol) and 6-(4- dimethylamino-cyclohex-1-enyl)-pyridin-2-ylamine, isomer 1 (preparation 10, 100 mg, 0.46 mmol) provides the free amine of the title compound as a colorless oil (78 mg, 45%): MS (ES): m/z=374.1 (M+H)$^+$; $^1$H NMR (CDCl$_3$): δ 9.03 (s, br, 1H), 8.26 (d, 1H), 7.73 (t, 1H), 7.30 (m, 1H), 7.19 (d, 1H), 7.09 (d, 1H), 6.98 (dt, 1H), 6.62 (m, 1H), 2.58 (m, 1H), 2.38 (m, 3H), 2.34 (s, 6H), 2.15 (m, 2H), 1.53 (m, 1H). Using a salt formation method similar to that in example 1 provides the di-hydrochloride salt.

Example 22

2,4-Dichloro-N-(6-(4-Dimethylamino-cyclohex-1-enyl)-pyridin-2-yl)-benzamide di-hydrochloride salt, isomer 1

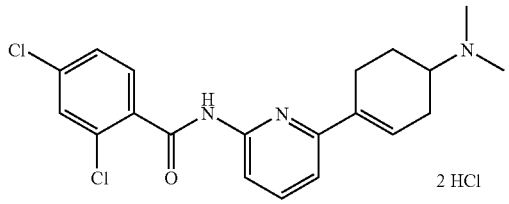

Using a method similar to example 1, using 2,4-dichlorobenzoyl chloride (126 mg, 0.60 mmol) and 6-(4-dimethylamino-cyclohex-1-enyl)-pyridin-2-ylamine, isomer 1 (preparation 10, 100 mg, 0.46 mmol) provides the free base of the title compound as a colorless oil (120 mg, 67%): MS (ES): m/z=390.1 (M+H)$^+$; $^1$H NMR (CDCl$_3$): δ 8.90 (s, br, 1H), 8.20 (d, 1H), 7.73 (t, 1H), 7.57 (d, 1H), 7.45 (d, 1H), 7.28 (dd, 1H), 7.14 (d, 1H), 6.63 (m, 1H), 2.67 (m, 1H), 2.44 (m, 3H), 2.36 (s, 6H), 2.15 (m, 2H), 1.54 (m, 1H). Di-hydrochloride salt: Anal. cal'd for C$_{20}$H$_{21}$Cl$_2$N$_3$O.2HCl: C, 51.86; H, 5.00; N, 9.07. Found: C, 51.78; H, 5.04; N, 8.99.

Example 23

2,4-Difluoro-N-(6-(4-Dimethylamino-cyclohex-1-enyl)-pyridin-2-yl)-benzamide di-hydrochloride salt

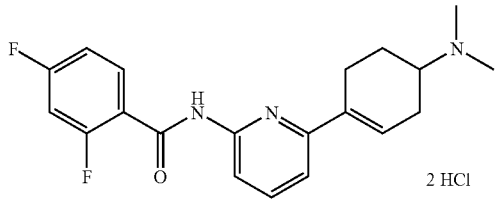

Using a method similar to example 1, using 2,4-difluorobenzoyl chloride (106 mg, 0.60 mmol) and 6-(4-dimethylamino-cyclohex-1-enyl)-pyridin-2-ylamine (preparation 10, 100 mg, 0.46 mmol) provides the free amine of the title compound as a colorless oil (59 mg, 36%): MS (ES): m/z=358.2 (M+H)$^+$; $^1$H NMR (CDCl$_3$): δ 8.94 (d, 1H), 8.21 (m, 2H), 7.72 (t, 1H), 7.19 (d, 1H), 7.04 (m, 2H), 6.71 (m, 1H), 2.78 (m, 1H), 2.49 (m, 3H), 2.38 (s, 6H), 2.17 (m, 2H), 1.59 (m, 1H). Using a salt formation method similar to that in example 1 gives the dihydrochloride salt: Di-hydrochloride salt: Anal cal'd for C$_{20}$H$_{21}$F$_2$N$_3$O.2HCl: C, 55.82; H, 5.39; N, 9.76. Found: C, 56.15; H, 5.49; N, 9.73.

Example 24

N-(6-(4-Dimethylamino-cyclohex-1-enyl)-pyridin-2-yl)-4-fluoro-benzamide hydrochloride salt, isomer 2

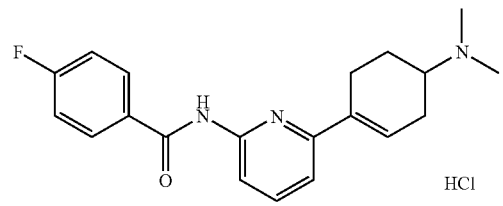

Combine 4-fluoro-benzoyl chloride (127 mg, 0.80 mmol), 6-(4-dimethylamino-cyclohex-1-enyl)-pyridin-2-ylamine, isomer 2 (preparation 11, 145 mg, 0.67 mmol), triethylamine (81 mg, 0.80 mmol) and 1,4-dioxane (6 mL) and heat at 55° C. for 15 hr. Dilute the mixture with DCM, wash with 0.1N NaOH solution. Extract the aqueous layer twice with DCM. Combine the organic layers, dry over sodium sulfate, filter and concentrate to give a residue. Purify the residue by chromatography (silica gel, 5% 2M NH$_3$/MeOH in DCM) to provide the free amine of the title compound as a slightly yellow oil (183 mg, 80%): MS (ES): m/z=340.1 (M+H)$^+$; $^1$H NMR (CDCl$_3$): δ 8.55 (s, br, 1H), 8.19 (d, 1H), 7.95 (m, 2H), 7.73 (t, 1H), 7.18 (m, 2H), 6.66 (m, 1H), 2.73 (m, 1H), 2.47 (m, 3H), 2.37 (s, 6H), 2.15 (m, 2H), 1.57 (m, 1H). Using a salt formation method similar to that in example 1 gives the hydrochloride salt: hydrochloride salt: Anal. cal'd for C$_{20}$H$_{22}$FN$_3$O.1.5HCl0.5H$_2$O: C, 59.59; H, 6.13; N, 10.42. Found: C, 59.71; H, 5.56; N, 10.31.

Example 25

2,4-Difluoro-N-(6-(4-Dimethylamino-cyclohex-1-enyl)-pyridin-2-yl)-benzamide hydrochloride salt, isomer 2

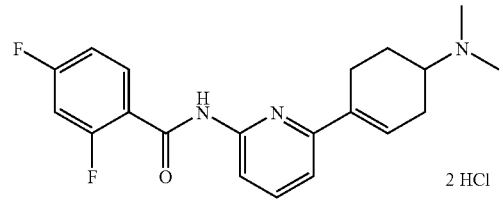

Using a method similar to example 24, using 2,4-difluorobenzoyl chloride (141 mg, 0.80 mmol) and 6-(4-dimethylamino-cyclohex-1-enyl)-pyridin-2-ylamine, isomer 2 (preparation 11, 145 mg, 0.67 mmol) provides the free amine of the title compound as a colorless oil (225 mg, 94%): MS (ES): m/z=358.1 (M+H)$^+$; $^1$H NMR (CDCl$_3$): δ 8.94 (d, 1H), 8.21 (m, 2H), 7.72 (t, 1H), 7.19 (d, 1H), 7.04 (m, 2H), 6.71 (m, 1H), 2.78 (m, 1H), 2.49 (m, 3H), 2.38 (s, 6H), 2.17 (m, 2H), 1.59 (m, 1H). Using a salt formation method similar to that in example 1 gives the dihydrochloride salt.

Example 26

2-Chloro-N-(6-(4-dimethylamino-cyclohex-1-enyl)-pyridin-2-yl)-benzamide hydrochloride salt, isomer 2

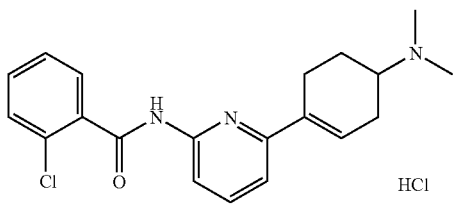

Using a method similar to example 24, using 2-chlorobenzoyl chloride (140 mg, 0.80 mmol) and 6-(4-dimethylamino-cyclohex-1-enyl)-pyridin-2-ylamine, isomer 2 (preparation 11, 145 mg, 0.67 mmol) provides the free amine of the title compound as a slightly yellow oil (218 mg, 91%): MS (ES): m/z=356.1 (M+H)$^+$; $^1$H NMR (CDCl$_3$): δ 8.69 (s, br, 1H), 8.22 (d, 1H), 7.67 (m, 2H), 7.45 (m, 3H), 7.15 (d, 1H), 6.64 (m, 1H), 2.69 (m, 1H), 2.45 (m, 3H), 2.36 (s, 6H), 2.13 (m, 2H), 1.56 (m, 1H). Using a salt formation method similar to that in example 1 gives the hydrochloride salt: Mono-hydrochloride salt: Anal. cal'd for C$_{20}$H$_{22}$ClN$_3$O.HCl.1.2H$_2$O: C, 57.91; H, 6.20; N, 10.13. Found: C, 58.18; H, 5.98; N, 9.74.

Example 27

2-Chloro-N-(6-(4-dimethylamino-cyclohex-1-enyl)-pyridin-2-yl)-6-fluoro-benzamide dihydrochloride salt, isomer 2

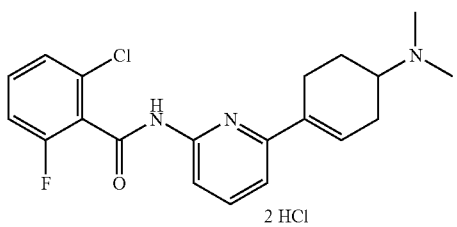

Using a method similar to example 1, using 2-chloro-6-fluoro-benzoyl chloride (134 mg, 0.69 mmol) and 6-(4-dimethylamino-cyclohex-1-enyl)-pyridin-2-ylamine, isomer 2 (preparation 11, 100 mg, 0.46 mmol) provides the free amine of the title compound as an oil (82 mg, 48%): MS (ES): m/z=374 (M+H)$^+$; $^1$H NMR (CD$_3$OD): δ 8.15 (t, 1H), 7.57 (m, 3H), 7.34 (d, 1H), 7.20 (t, 1H), 6.71 (m, 1H), 3.52 (m, 1H), 2.86 (s, 6H), 2.69 (m, 4H), 2.35 (m, 1H), 1.87 (m, 1H). Using a salt formation method similar to that in example 1 gives the dihydrochloride salt.

Example 28

N-(6-(4-Dimethylamino-cyclohex-1-enyl)-pyridin-2-yl)-2,4-difluoro-benzamide dihydrochloride salt, isomer 2

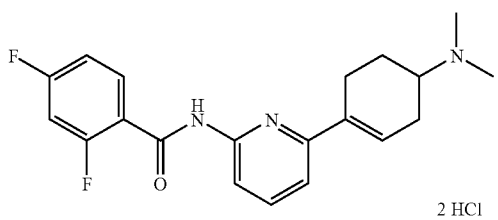

Using a method similar to example 1, using 2,4-difluoro-benzoyl chloride (122 mg, 0.69 mmol) and 6-(4-dimethylamino-cyclohex-1-enyl)-pyridin-2-ylamine (preparation 11, 100 mg, 0.46 mmol) provides the free amine of the title compound as an oil (52 mg, 32%): MS(ES): m/z=358 (M+H)$^+$; $^1$H NMR (CD$_3$OD): δ 8.23 (t, 1H), 7.89 (m, 1H), 7.64 (m, 2H), 7.14 (m, 2H), 6.74 (m, 1H), 3.52 (m, 1H), 2.86 (s, 6H), 2.69 (m, 4H), 2.35 (m, 1H), 1.87 (m, 1H). Using a salt formation method similar to that in example 1 gives the dihydrochloride salt.

Example 29

2-Bromo-N-(6-(4-dimethylamino-cyclohex-1-enyl)-pyridin-2-yl)-benzamide dihydrochloride salt, isomer 2

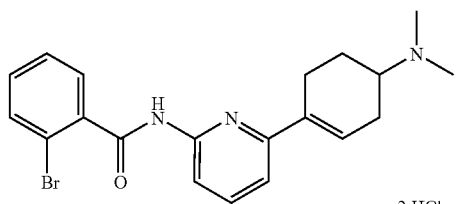

Using a method similar to example 1, using 2-bromobenzoyl chloride (151 mg, 0.69 mmol) and 6-(4-dimethylamino-cyclohex-1-enyl)-pyridin-2-ylamine, isomer 2 (preparation 11, 100 mg, 0.46 mmol) provides the free amine of the title compound as an oil (63 mg, 34%): MS (ES): m/z=400 (M+H)$^+$, 403 (M+3); $^1$H NMR (CD$_3$OD): δ 8.30 (t, 1H), 7.69 (d, 2H), 7.67 (d, 1H), 7.49 (m, 3H), 6.78 (m, 1H), 3.55 (m, 1H), 2.87 (s, 6H), 2.73 (m, 4H), 2.37 (m, 1H), 1.87 (m, 1H). Using a salt formation method similar to that in example 1 gives the dihydrochloride salt.

Example 30

N-(6-(4-Dimethylamino-cyclohex-1-enyl)-pyridin-2-yl)-2,4,6-trifluoro-benzamide dihydrochloride salt, isomer 2

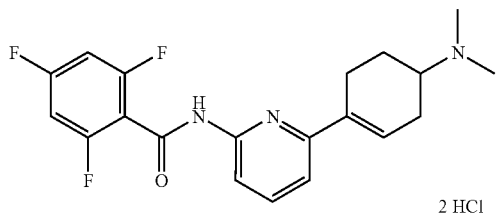

Using a method similar to example 1, using 2,4,6-trifluoro-benzoyl chloride (134 mg, 0.69 mmol) and 6-(4-dimethylamino-cyclohex-1-enyl)-pyridin-2-ylamine, isomer 2 (preparation 11, 100 mg, 0.46 mmol) provides the free amine of the title compound as an oil (80 mg, 46%): MS (ES): m/z=376.2 (M+H)$^+$; $^1$H NMR (CD$_3$OD): δ 8.25 (t, 1H), 7.67 (d, 1H), 7.74 (d, 1H), 7.12 (t, 2H), 6.81 (m, 1H), 3.62 (m, 1H), 2.96 (s, 6H), 2.73 (m, 4H), 2.45 (m, 1H), 1.95 (m, 1H). Using a salt formation method similar to that in example 1 gives the dihydrochloride salt.

Example 31

2-Chloro-N-(6-(4-dimethylamino-cyclohex-1-enyl)-pyridin-2-yl)-4-fluoro-benzamide dihydrochloride salt, isomer 2

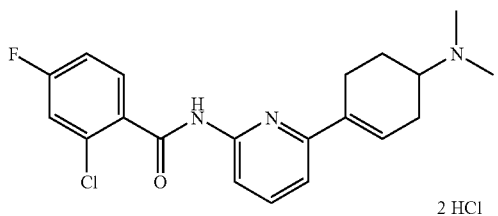

2 HCl

Using a method similar to example 1, using 2-chloro-4-fluoro-benzoyl chloride (133 mg, 0.69 mmol) and 6-(4-dimethylamino-cyclohex-1-enyl)-pyridin-2-ylamine, isomer 2 (preparation 11, 100 mg, 0.46 mmol) provides the free amine of the title compound as an oil (110 mg, 64%): MS (ES): m/z=374.2 (M+H)$^+$; $^1$H NMR (CD$_3$OD): δ 8.36 (t, 1H), 7.73 (m, 3H), 7.47 (d, 1H), 7.32 (t, 1H), 6.86 (m, 1H), 3.62 (m, 1H), 2.97 (s, 6H), 2.74 (m, 4H), 2.47 (m, 1H), 1.99 (m, 1H). Using a salt formation method similar to that in example 1 gives the dihydrochloride salt.

The compounds of this invention are useful for increasing activation of the 5-HT$_{1F}$ receptor. An increase in the activation of the 5-HT$_{1F}$ is useful for treating a variety of disorders which have been linked to decreased neurotransmission of serotonin in mammals, e.g., migraine headaches. See U.S. Pat. No. 5,708,008 demonstrating the nexus between activation of the 5-HT$_{1F}$ receptor and migraine. 5-HT$_{1F}$ receptor binding affinity is determined to demonstrate the use of the compounds of the present invention in the treatment of migraine. The ability of the compounds of this invention to bind to the 5-HT$_{1F}$ receptor subtype is measured essentially as described in N. Adham, et al., *Proceedings of the National 15 Academy of Sciences (USA)*, 90:408-412, 1993.

Membrane Preparation:

Prepare membranes from transfected Ltk-cells (transfected with the human 5-HT$_{1F}$ receptor sequence) that have grown to 100% confluency. Wash the cells twice with phosphate-buffered saline, scrape them from the culture dishes into 5 mL of ice-cold phosphate-buffered saline, and centrifuge at 200×g for 5 min. at 4° C. Resuspend the pellet in 2.5 mL of ice-cold Tris buffer (20 mM Tris HCl, pH 7.4 at 23° C., 5 mM EDTA) and homogenize with a Wheaton tissue grinder. Centrifuge the lysate at 200×g for 5 min. at 4° C. to pellet large fragments which are discarded. Collect the supernatant and centrifuge at 40,000×g for 20 min. at 4° C. Wash the resulting pellet once in ice-cold Tris wash buffer and resuspend in a final buffer containing 50 mM Tris HCl and 0.5 mM EDTA, pH 7.4 at 23° C. Maintain the membrane preparations on ice and utilize them for the radioligand binding assays within two hr. of preparation. Determine protein concentrations by the method of Bradford. *Anal. Biochem.*, 72:248-254, 1976.

Radioligand Binding:

($^3$H) 5-HT binding is performed using slight modifications of the 5-HT$_{1D}$ assay conditions reported by Herrick-Davis and Titeler (*J. Neurochem.*, 50:1624-1631, 1988) with the omission of masking ligands. Conduct radioligand binding studies at 37° C. in a total volume of 250 μL of buffer (50 mM Tris, 10 mM MgCl$_2$, 0.2 mM EDTA, 10 μM pargyline, 0.1% ascorbate, pH 7.4 at 37° C.) in 96 well microtiter plates. Perform saturation studies using ($^3$H) 5-HT at 12 different concentrations ranging from 0.5 nM to 100 nM. Perform displacement studies using 4.5-5.5 nM ($^3$H) 5-HT. Use 6-12 concentrations of compound to obtain binding profiles of drugs in competition experiments. Incubations are for 30 minutes for both saturation and displacement studies based upon initial investigations which determined equilibrium binding conditions. Define nonspecific binding in the presence of 10 μM 5-HT. Initiate binding by the addition of 50 μL membrane homogenate (10-20 μg). Terminate the reaction by rapid filtration through presoaked (0.5% poylethyleneimine) filters using 48R Brandel Cell Harvester (Gaithersburg, Md.). Wash the filters for 5 seconds with ice cold buffer (50 mM Tris HCl, pH=7.4 at 4° C.), dry the filters, and place them individually into vials containing 2.5 mL Readi-Safe (Beckman, Fullerton, Calif.) and radioactivity was measured using a Beckman LS 5000TA liquid scintillation counter. The efficiency of counting of ($^3$H) 5-HT averages between 45-50%. Analyze the binding data by computer-assisted nonlinear regression analysis (Accufit and Accucomp, Lunden Software, Chagrin Falls, Ohio). Convert the IC$_{50}$ values to K$_i$ values using the Cheng-Prusoff equation. *Biochem. Pharmacol.*, 22:3099-3108 (1973). Perform experiments in triplicate. Representative compounds of the present invention were assayed essentially as described above and were found to have high affinity for the 5-HT$_{1F}$ receptor, as for example K$_i$'s of less than or equal to about 700 nM. Preferred compounds of the present invention have K$_i$'s of less than or equal to about 300 nM. Yet more preferred compounds are those having a K$_i$ of less than or equal to about 200 nM. Particularly preferred compounds are those having a K$_i$ of less than or equal to about 50 nM. Exemplified compounds have K$_i$'s of less than or equal to about 50 nM.

Measurement of cAMP Formation

As was reported by R. L. Weinshank, et al., WO93/14201, the 5-HT$_{1F}$ receptor is functionally coupled to a G-protein as measured by the ability of serotonin and serotonergic drugs to inhibit forskolin stimulated cAMP production in NIH3T3 cells transfected with the 5-HT$_{1F}$ receptor. Adenylate cyclase activity is determined using standard techniques. A maximal effect is achieved by serotonin. An E$_{max}$ is determined by dividing the inhibition of a test compound by the maximal effect and determining a percent inhibition. N. Adham, et al., supra,; R. L. Weinshank, et al., *Proceedings of the National Academy of Sciences (USA)*, 89:3630-3634, 1992; and the references cited therein.

Incubate human 5-HT$_{1F}$ receptor transfected NIH3T3 cells (estimated B$_{max}$ from one point competition studies=488 fmol/mg of protein) in DMEM, 5 mM theophylline, 10 mM HEPES (4-(2-hydroxyethyl)-1-piperazineethanesulfonic acid) and 10 μM pargyline for 20 minutes at 37° C., 5% CO$_2$. Use a range of 6 final concentrations of test compound in parallel incubations to obtain drug dose-effect curves. Obtain a dose-response curve for 5-HT measured in parallel, using a fixed dose of methiothepin (0.32 μM), for use in demonstrating competitive antagonism. Add the test compound or 5-HT to the cells, and follow immediately with the addition of forskolin (10 μM) to initiate stimulated cAMP production. Incubate the cells for 10 minutes at 37° C., 5% CO$_2$. Aspirate the medium and quench the reaction with 100 mM HCl. Cool the plates at 4° C. for 15 min., centrifuge to pellet cellular debris (5 min., 500×g), aliquot the supernatant into vials and store at −20° C. until assessment of cAMP formation by radioimmunoassay (cAMP radioimmunoassay kit; Advanced Magnetics, Cambridge, Mass.). Quantify radioactivity using a Packard COBRA Auto Gamma counter, equipped with data reduction software. Representative compounds of the present invention are assayed essentially as described above and are found to be agonists of the 5-HT1F receptor.

Dural Protein Extravasation Assay

The inhibition of dural protein extravasation is a functional assay for the neuronal mechanism of migraine. A compound's ability to inhibit dural protein extravasation can be tested as described in the following assay.

Anesthetize Harlan Sprague-Dawley rats (225-325 g) or guinea pigs from Charles River Laboratories (225-325 g) with sodium pentobarbital (intraperitoneal injection, 65 mg/kg or 45 mg/kg, respectively). For each animal, place the animal in a stereotaxic frame (David Kopf Instruments) with the incisor bar set at −3.5 mm for rats or −4.0 mm for guinea pigs. Make a midline sagital scalp incision, and drill two pairs of bilateral holes through the skull (6 mm posteriorly, 2.0 and 4.0 mm laterally on both sides of the mid-line in rats; 4 mm posteriorly and 3.2 and 5.2 mm laterally on both sides of the mid-line in guinea pigs, all coordinates referenced to bregma.). Lower pairs of stainless steel stimulating electrodes, insulated except at the ends (Rhodes Medical Systems, Inc.), through the holes in both hemispheres, one electrode to a hole, to a depth of 9 mm (rats) or 10.5 mm (guinea pigs) from dura.

Expose the femoral vein and inject a dose of the test compound or saline negative control intravenously (1 mL/kg). Approximately 7 min. later, inject a 50 mg/kg dose of Evans Blue intravenously. The Evans Blue is a fluorescent dye which complexes with proteins in the blood and functions as a marker for dural protein extravasation. Exactly 10 min. post-injection of the test compound, stimulate the left trigeminal ganglion for 3 min. at a current intensity of 1.0 mA (5 Hz, 4 msec duration) with a Model 273 potentiostat/galvanostat (EG&G Princeton Applied Research).

Fifteen minutes following stimulation, kill the animal by exsanguination with 20 mL of saline. Remove the top of the skull to facilitate the collection of dural membrane samples. Remove the membrane samples from both hemispheres, rinse with water, spread flat on microscope slides, dry the tissue on a microscope slide warmer, and apply a coverslip with a 70% glycerol/water solution.

Quantify the amount of Evans Blue dye in each sample using a fluorescence microscope (Zeiss) equipped with a grating monochronomator, a spectrophotometer, a computer-driven motorized stage, and an interface to a personal computer. For each dural membrane sample, measure fluorescence at 25 points (500 μm steps covering a 2.5×2.5 mm square area) using an excitation wavelength of approximately 535 nm and measuring the emission intensity at a wavelength of 600 nm. Determined the mean and standard deviation of these measurements.

The extravasation induced by the electrical stimulation of the trigeminal ganglion is an ipsilateral effect (i.e. occurs only on the side of the dura in which the trigeminal ganglion was stimulated). This allows the stimulated dura to be used as the test tissue and the unstimulated half of the dura to be used as a control. The ratio of the amount of extravasation in the dura from the stimulated side compared to the unstimulated side is calculated. Saline controls yield a ratio of approximately 2.0 in rats and 1.8 in guinea pigs. In contrast, a compound which effectively prevents the extravasation in the dura from the stimulated side will have a ratio of approximately 1.0. Using a range of compound doses and multiple animals at each dosage level, generate a dose-response curve for the test compound and approximate the dose that inhibits the extravasation by 50% ($ID_{50}$). Representative compounds of the present invention are assayed essentially as described above. The compounds are found to significantly inhibit dural protein extravasation and are thus efficatious in the neurogenic plasma protein extravasation model for migraine.

Rabbit Saphenous Vein Contraction

Sacrifice male New Zealand White rabbits (3-6 lbs) (Hazleton, Kalamazoo, Mich.) by a lethal dose of sodium pentobarbital (325 mg) injected into the ear vein. Dissect saphenous vein tissue free of connective tissue, cannulate in situ with polyethylene tubing (PE50, outside diameter=0.97 mm) and place in petri dishes containing modified Kreb's solution (118.2 mMol NaCl, 4.6 mMol KCl, 1.6 mMol $CaCl_2 \cdot H_2O$, 1.2 mMol $KH_2PO_4$, 1.2 mMol $MgSO_4$, 10.0 mMol dextrose and 24.8 mMol $NaHCO_3$). Bend the tips of two 30-gauge stainless steel hypodermic needles into an L-shape and slip them into the lumen of the polyethylene tubing. Gently push vein tissue from the cannula onto the needles. Separate the needles and attach the lower needle with thread to a stationary glass rod and the upper needle with thread to a force transducer (Statham UC-3).

Mount the tissues in organ baths containing 10 mL of modified Krebs' solution. Maintain tissue bath solutions at 37° C. and aerate with 95% $O_2$ and 5% $CO_2$. Apply an initial optimum resting force of 4 grams to the vein tissue. Record isometric contractions as changes in grams of force on a Beckman Dynograph with Statham UC-3 transducers and microscale accessory attachments. Allow tissues to equilibrate 1 to 2 hr. before exposure to test compound. Add 67 mM KCl to the bath and record the maximal contraction. Flush the bath, allow the tissue to re-equilibrate under a 4 gram force, add test compound and record the force of contraction. Add additional compound to achieve the next concentration in a range of compound concentrations to generate cumulative agonist concentration-response curves for each test compound. Tissues can be used to generate up to two agonist concentration-response curves. Calculate the mean $EC_{50}$ and the maximal compound response, which maximum is expressed as a percentage of the maximal contraction for the tissue in response to the 67 mM KCl administered initially to each tissue.

Two important parameters can be measured with this vasoconstriction assay, saphenous vein contraction ($EC_{50}$) and maximal contraction as a percentage of the maximal KCl response ($\%_{max}$ KCl). The saphenous vein contraction ($EC_{50}$) is a measure of the dose required to contract tissue to 50% of the maximal response that the specific compound is capable of mediating. The maximal response that the saphenous vein is capable of exhibiting is measured after administration of a high concentration (67 mM) of KCl. The $\%_{max}$ KCl contraction is the ratio of the maximal response that the specific compound is capable of mediating divided by the maximal response that the tissue can produce upon stimulation with KCl. For purposes of this application, a compound may be considered to not have significant vasoconstrictive activity if it produces a maximal contraction of less than or equal to 5% of the contraction produced by the 67 mM KCl positive control at a compound concentration of up to 100 μM, when assayed essentially as described above.

Representative compounds of the present invention are tested for vasoconstrictive activity in the rabbit saphenous vein assay essentially as described above and are found to not be significantly vasoconstrictive. All compounds of the present invention that were tested had a $\%_{max}$ KCl less than or equal to 10%. This contrasts greatly with prior art compounds for the treatment of migraine targeting the neural vasoconstrictive model for migraine treatment, which compounds were selected on the basis of strong vasoconstrictive activity, as for example, sumatriptan, which has an $EC_{50}$ of 0.66 mM and a $\%_{max}$ KCl of 64.20 when tested essentially as described above.

Selectivity for the 5-$HT_{1F}$ Receptor

Compounds of the prevent invention are relatively selective for the 5-$HT_{1F}$ receptor, particularly in comparison to other 5-HT receptor subtypes, specifically other receptors in the 5-HT$_1$ subclass, as for example, but without limitation, the 5-HT$_{1A}$, 5-HT$_{1B}$, 5-HT$_{1D}$, and 5-HT$_{1E}$ receptor subtypes. Affinity for these other receptor subtypes can readily be determined by slight modification of the above described radioligand receptor binding assays using cells transfected with the desired receptor subtype in place of cells transfected with the 5-HT$_{1F}$ receptor subtype. The binding affinities of representative compounds of the present invention were determined by such assays and were found to be selective for the 5-HT$_{1F}$ receptor; that is the affinity of the compounds for the 5-HT$_{1F}$ receptor was on the whole, higher than for other receptor subtypes, particular for the 5-HT$_{1B}$ and 5-HT$_{1D}$ receptor subtypes.

Specificity Index

The specificity of compounds of the present invention for 5-HT$_{1F}$ mediated inhibition of dural protein extravasation versus vasoconstrictive activity can be expressed with a Specificity Index, which is the ratio of vasoconstriction to efficacy in inhibiting dural protein extravasation:

$$\text{Specificity Index} = \frac{\text{Corrected Vasoconstriction } EC_{50}(M)}{\text{Extravasation } ID_{50}(\text{mMol/kg})}$$

The Corrected Vasoconstriction takes into consideration the maximal contraction relative to KCl for each individual compound, and is defined as the vasoconstriction EC$_{50}$ value divided by the %$_{max}$ KCl.

For example, sumatriptan has a corrected vasoconstriction EC$_{50}$ of 1.03×10$^{-8}$ M (0.66 mM EC$_{50}$÷64.20%$_{max}$ KCl) and an extravasation inhibition ID$_{50}$ of 2.6×10$^{-8}$ mMol/Kg, giving a Specificity Index of 0.40.

Thus the procedure for determining the Specificity Index of any given compound is as follows:

1. Measure the affinity of the compound for the 5-HT$_{1F}$ receptor using the radioligand binding method described above;

2. Once affinity for the 5-HT$_{1F}$ receptor is established, determine whether the compound is an agonist, partial agonist or antagonist of the 5-HT$_{1F}$ receptor by its response in the above described cAMP assay;

3. If the compound is shown to be an agonist or partial agonist with an E$_{max}$ of at least about 50%, measure efficacy of the compound in inhibition of dural protein extravasation and saphenous vein contraction using the above described assays; and 4. Calculate the Specificity Index as shown above.

While compounds with a Specificity Index greater than 1 are useful for the methods and uses of the present invention, larger values for the Specificity Index are preferred. A larger Specificity Index indicates greater specificity for efficacy in inhibition of dural protein extravasation over vasoconstriction. Thus, preferred compounds have a Specificity Index of greater than or equal to 10 (at least 10), preferably greater than or equal to 100 (at least 100). More preferred compounds have a Specificity Index of greater than or equal to 1000 (at least 1000), and yet more preferred compounds have Specificity Indexes greater than or equal to 5000 (at least 5000).

Pharmaceutical Compositions

The type of pharmaceutical composition used for the administration of the compounds employed in the methods of the present invention may be dictated by the particular compounds selected, the type of pharmacokinetic profile desired from the route of administration, and the state of the patient.

Pharmaceutical compositions amenable to oral, sublingual, nasal or injectable administration are prepared in a manner well known in the pharmaceutical art and comprise at least one active compound. See, e.g., REMINGTON'S PHARMACEUTICAL SCIENCES, (16th ed. 1980)

In general, a pharmaceutical composition of the present invention includes an active ingredient (a compound of formula I) and is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, gels, suppositories, sterile injectable solutions, and sterile packaged powders.

In preparing a pharmaceutical composition, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the pharmaceutical composition, e.g., about 40 mesh. In one embodiment of the present invention, the particle size range is between about 0.1 μm to about 100 μm.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The pharmaceutical compositions can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compounds of the invention can be formulated so as to provide quick, sustained or delayed release of the active ingredient after administration to the patient by employing procedures known in the art.

While it is possible to administer a compound employed in the methods of this invention directly without any formulation, the compounds are usually administered in the form of pharmaceutical compositions comprising a pharmaceutically acceptable excipient and at least one active ingredient. These formulations can be administered by a variety of routes including oral, buccal, rectal, intranasal, transdermal, subcutaneous, intravenous, intramuscular, and intranasal. Many of the compounds employed in the methods of this invention are effective as both injectable and oral compositions.

In order to administer transdermally, a transdermal delivery device ("patch") is needed. Such transdermal patches may be used to provide continuous or discontinuous infusion of a compound of the present invention in controlled amounts. The construction and use of transdermal patches for the delivery of pharmaceutical agents is well known in the art. See, e.g., U.S. Pat. No. 5,023,252. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, which is herein incorporated by reference. The delivery of hydrophilic drugs may be enhanced by intra-arterial infusion of hypertonic solutions, which can transiently open the blood-brain barrier.

In one preferred embodiment of the present invention, there is provided a pharmaceutical composition comprising at lest one compound as described above in a pharmaceutical composition adapted for buccal and/or sublingual, or nasal administration. This embodiment provides administration of the active compound in a manner that avoids gastric complications, such as first pass metabolism by the gastric system and/or through the liver. This administration route may also reduce adsorption times, providing more rapid onset of therapeutic benefit. The compounds of the present invention may provide particularly favorable solubility profiles to facilitate sublingual/buccal pharmaceutical compositions. Such pharmaceutical compositions typically require relatively high concentrations of active ingredients to deliver sufficient amounts of active ingredients to the limited surface area of the sublingual/buccal mucosa for the relatively short durations the pharmaceutical composition is in contact with the surface area, to allow the absorption of the active ingredient. Thus, the very high activity of the compounds of the present invention facilitate their suitability for sublingual/buccal pharmaceutical compositions.

A compound of formula I is preferably formulated in a unit dosage form, each dosage containing from about 0.001 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient as described above.

The compounds of the present invention are generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

We claim:
1. A compound of formula I:

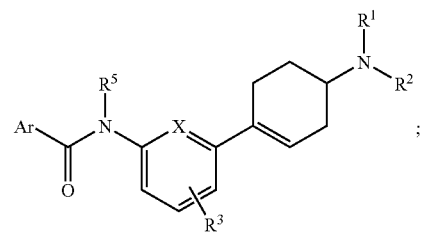

or a pharmaceutically acceptable acid addition salt thereof, where;

X is —C($R^4$)═ or —N═;

Ar is phenyl, substituted phenyl, heterocycle, or substituted heterocycle;

$R^1$ and $R^2$ are independently hydrogen or $C_1$-$C_3$ alkyl;

$R^3$ is hydrogen, fluoro, or methyl;

when X is —C($R^4$)═, $R^4$ is hydrogen, fluoro, or methyl, provided that no more than one of $R^3$ and $R^4$ may be other than hydrogen; and $R^5$ is hydrogen, methyl, or ethyl.

2. The compound according to claim 1 wherein Ar is phenyl or substituted phenyl.

3. The compound according to claim 2 wherein Ar is substituted phenyl and wherein the phenyl group is substituted with one to three halo substituents; or substituted with one to two substituents independently selected from the group consisting of halo, $C_1$-$C_4$ alkyl, $C_1$-$C_4$ alkoxy, $C_1$-$C_4$ alkylthio, cyano, and nitro, wherein each alkyl, alkoxy and alkylthio substituent can be further substituted independently one to five halo groups each independently selected from fluoro and chloro.

4. The compound according to claim 2 wherein Ar is substituted phenyl and wherein the phenyl group is substituted with 1 to 3 halo groups.

5. The compound according to claim 1 wherein Ar is heterocycle or substituted heterocycle, wherein the heterocycle is selected from the group consisting of furanyl, thiophenyl, pyrrolyl, pyridinyl, N-methylpyrrolyl, pyrimidinyl, pyrazinyl, benzofuranyl, benzothiophenyl, and indolyl; and wherein substituted heterocycle is taken to mean the ring moiety is substituted with one to three halo substituents; or substituted with one to two substituents independently selected from the group consisting of halo, $C_1$-$C_4$ alkyl, $C_1$-$C_4$ alkoxy, $C_1$-$C_4$ alkylthio, cyano, and nitro, wherein each alkyl, alkoxy and alkylthio substituent can be further substituted independently one to five halo groups each independently selected from fluoro and chloro.

6. The compound according to claim 1 wherein $R^5$ is hydrogen.

7. The compound according to claim 1 wherein $R^1$ and $R^2$ are methyl.

8. A pharmaceutical composition comprising a compound according to claim 1 and a pharmaceutical carrier, diluent, or excipient.

9. A method for the treatment or prevention of migraine in a mammal comprising administering to a mammal in need of such treatment or prevention an effective amount of a compound of formula I:

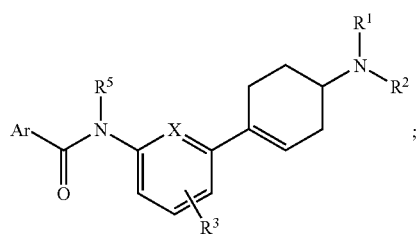

or a pharmaceutically acceptable acid addition salt thereof, where;

X is $-C(R^4)=$ or $-N=$;

Ar is phenyl, substituted phenyl, heterocycle, or substituted heterocycle;

$R^1$ and $R^2$ are independently hydrogen or $C_1$-$C_3$ alkyl;

$R^3$ is hydrogen, fluoro, or methyl;

when X is $-C(R^4)=$, $R^4$ is hydrogen, fluoro, or methyl, provided that no more than one of $R^3$ and $R^4$ may be other than hydrogen; and $R^5$ is hydrogen, methyl, or ethyl.

10. The method according to claim 9 wherein the mammal is a human.

* * * * *